(12) United States Patent
Miller

(10) Patent No.: US 7,326,170 B1
(45) Date of Patent: Feb. 5, 2008

(54) METHOD AND APPARATUS FOR RESTORING OR ENHANCING AN AMBIENT MAGNETIC FIELD

(76) Inventor: Wendell E. Miller, 1907 Crescent Dr., Warsaw, IN (US) 46580

( * ) Notice: Subject to any disclaimer, the term of this patent is extended or adjusted under 35 U.S.C. 154(b) by 734 days.

(21) Appl. No.: 10/454,881

(22) Filed: Jun. 5, 2003

Related U.S. Application Data

(63) Continuation-in-part of application No. 09/755,697, filed on Jan. 5, 2001, now abandoned, which is a continuation-in-part of application No. 09/336,271, filed on Jun. 18, 1999, now Pat. No. 6,203,486.

(60) Provisional application No. 60/254,739, filed on Dec. 11, 2000.

(51) Int. Cl.
*A61N 2/00* (2006.01)
(52) U.S. Cl. .......................................... 600/9
(58) Field of Classification Search ............. 600/9–15
See application file for complete search history.

(56) References Cited

U.S. PATENT DOCUMENTS

| | | | |
|---|---|---|---|
| 3,764,539 A | 10/1973 | Cochardt et al. | |
| 3,921,620 A | 11/1975 | Nakayama | |
| 4,480,596 A | 11/1984 | Shumiyashu | |
| 4,489,711 A | 12/1984 | Latzke | |
| 4,587,956 A | 5/1986 | Griffin et al. | |
| 4,798,194 A | 1/1989 | Amishima | |
| 4,993,413 A | 2/1991 | McLeod et al. | |
| 5,045,050 A | 9/1991 | Liboff et al. | |
| 5,084,003 A | 1/1992 | Susic | |
| 5,226,185 A | 7/1993 | Guay et al. | |
| 5,277,692 A | 1/1994 | Ardizzone | |
| 5,295,494 A | 3/1994 | Rodriguez | |
| 5,351,389 A | 10/1994 | Erickson et al. | |
| 5,437,600 A | 8/1995 | Liboff et al. | |
| 5,450,859 A | 9/1995 | Litovitz | |
| 5,544,665 A | 8/1996 | Litovitz et al. | |
| 5,586,064 A | 12/1996 | Grupp | |
| 5,665,049 A | 9/1997 | Markoll | |
| 5,700,234 A | 12/1997 | Masuda | |
| 5,782,743 A | 7/1998 | Russell | |
| 5,788,624 A | 8/1998 | Lu et al. | |
| 5,807,233 A | 9/1998 | Sakuma et al. | |
| 5,817,000 A | 10/1998 | Souder | |
| 6,001,055 A | 12/1999 | Souder | |
| 6,126,588 A | 10/2000 | Flamant et al. | |
| 6,163,889 A | 12/2000 | Tate | |
| 6,203,486 B1 | 3/2001 | Miller et al. | |
| 6,258,020 B1 | 7/2001 | Lopez | |
| 6,267,720 B1 | 7/2001 | Knox et al. | |
| 6,749,596 B2 * | 6/2004 | Gray ......................... | 604/500 |

* cited by examiner

*Primary Examiner*—John P. Lacyk
(74) *Attorney, Agent, or Firm*—Wendel E. Miller, Patent Agent

(57) ABSTRACT

Apparatus and method are provided for enhancing the earth's dc magnetic field (14) and/or for restoring the earth's dc magnetic field (14), when the earth's dc magnetic field (14) has been degraded by steel construction, or has been degraded by either an extra-low-frequency or an rf magnetic field (96), in a living space (144). Magnetic-field enhancing/restoring apparatus includes beds (120), mattresses (314), bassinets (428), other seating furniture (370), office furniture (414), rooms (186), buildings (222), child-restraint seating (560), and vehicles (712). Apparatus and method also are provided for enhancing the earth's dc magnetic field in a body member (608) by use of body-worn apparatus (596). Magnetic-field enhancers/restorers include magnetic-field-enhancing coils (226) and magnetized sheets or pads (514).

27 Claims, 10 Drawing Sheets

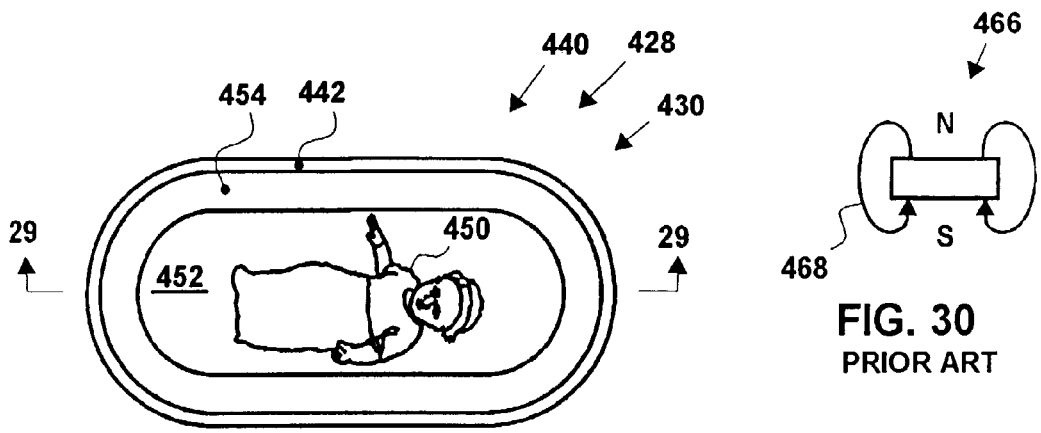
FIG. 28
FIG. 30
PRIOR ART
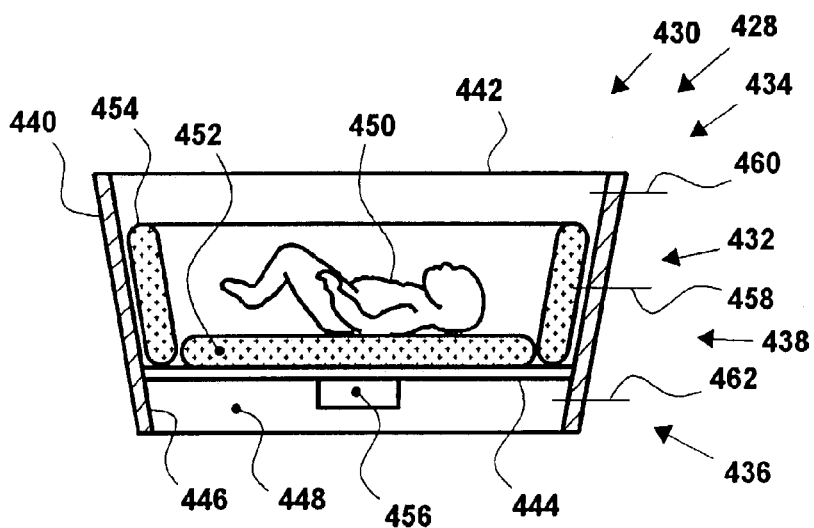
FIG. 29
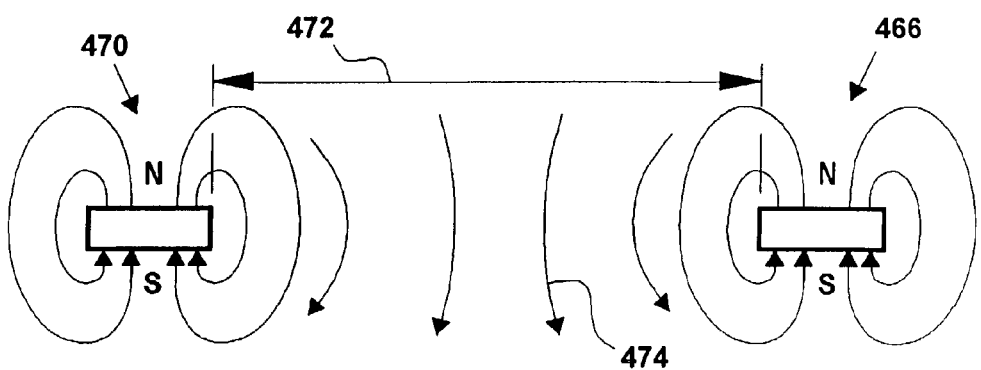
FIG. 31

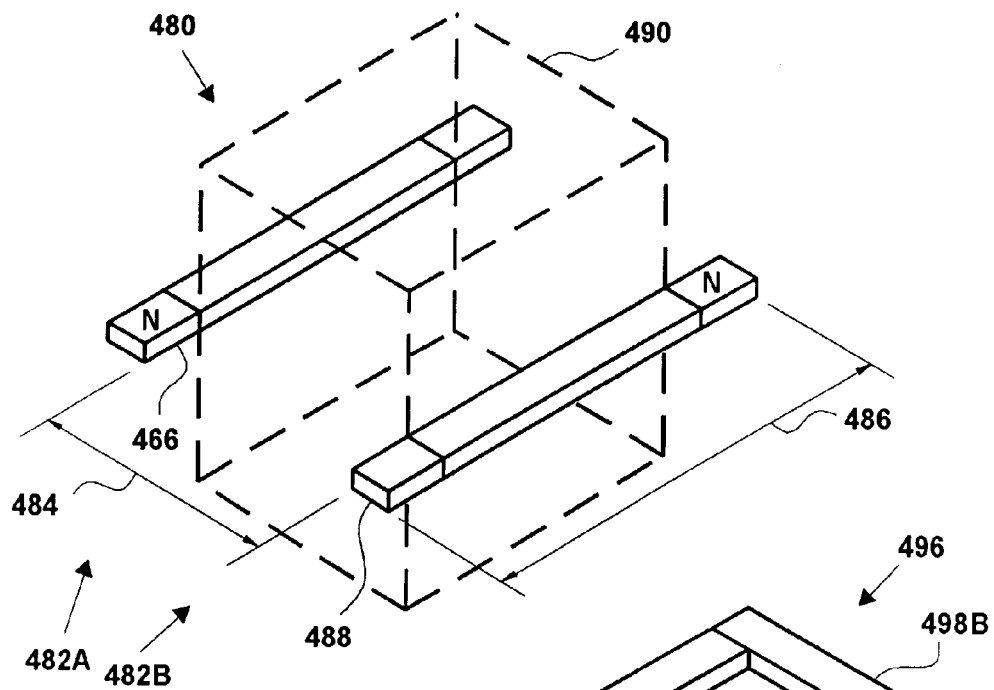
FIG. 32
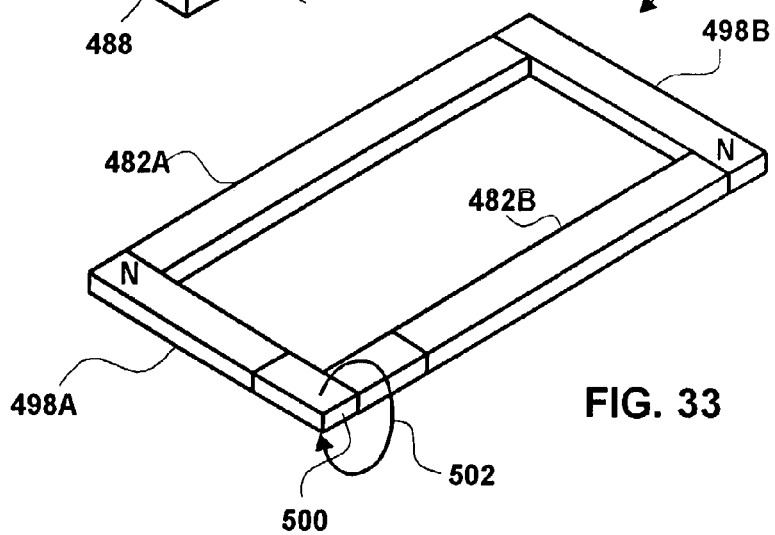
FIG. 33
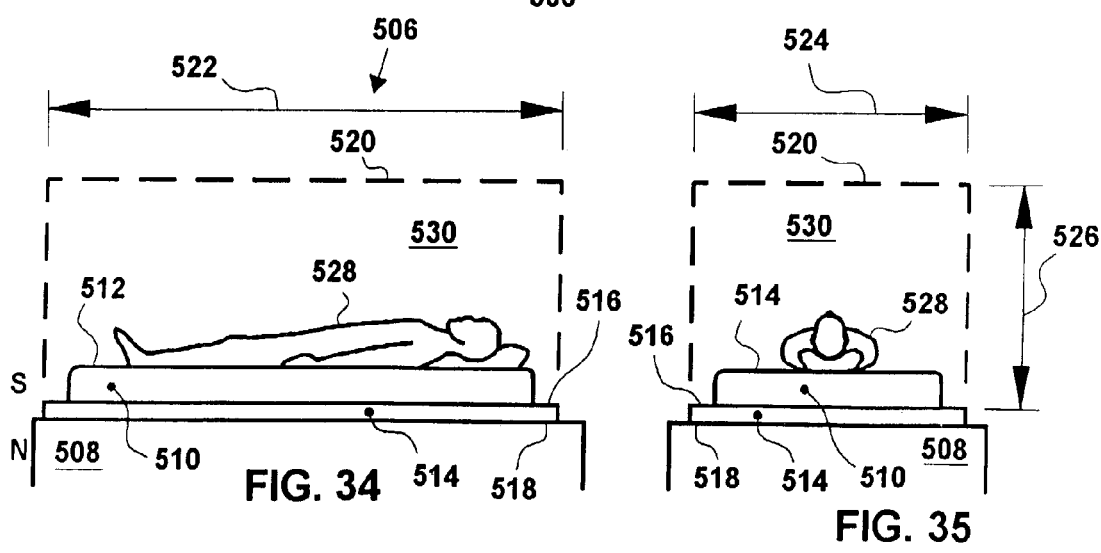
FIG. 34
FIG. 35

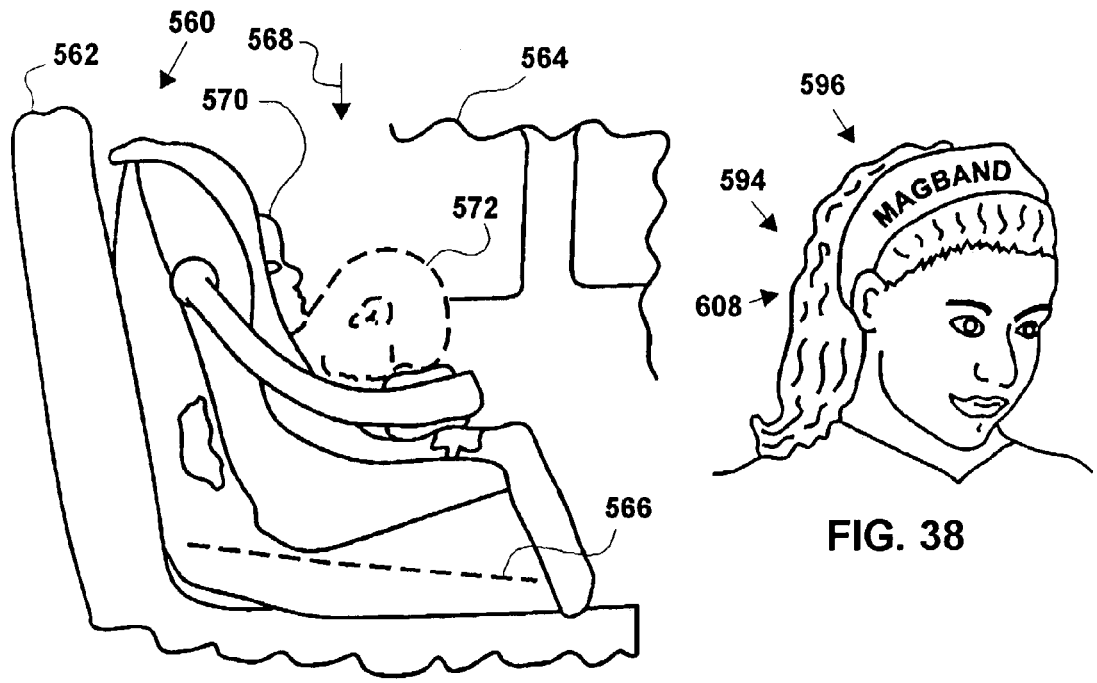
FIG. 36
FIG. 38
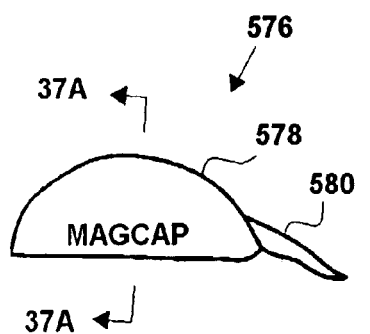
FIG. 37
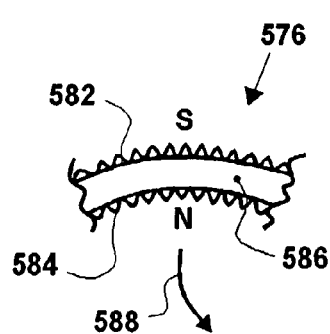
FIG. 37A
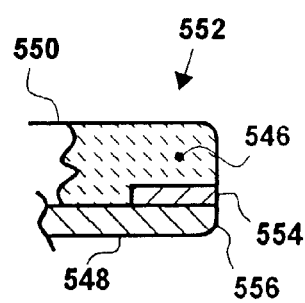
FIG. 35D
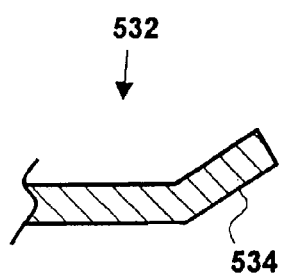
FIG. 35A
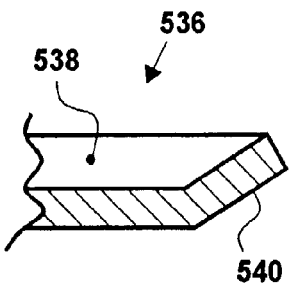
FIG. 35B
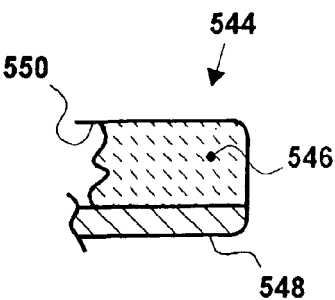
FIG. 35C

METHOD AND APPARATUS FOR RESTORING OR ENHANCING AN AMBIENT MAGNETIC FIELD

CROSS-REFERENCES TO RELATED APPLICATIONS

This patent application is a Continuation-in-part of U.S. patent application Ser. No. 09/755,697, filed Jan. 5, 2001 now abandoned, which is a Continuation-in-part of U.S. patent application Ser. No. 09/336,271, filed Jun. 18, 1999, which issued as U.S. Pat. No. 6,203,486 on Mar. 20, 2001. This Continuation-in-part Application also claims priority of Provisional Patent Application No. 60/254,739, filed Dec. 11, 2000.

STATEMENT RE FEDERALLY SPONSORED RESEARCH OR DEVELOPMENT

Not Applicable

REFERENCE TO A "SEQUENCE LISTING"

Not Applicable

BACKGROUND OF THE INVENTION

1. Field of the Invention

The present invention relates generally to magnetic fields. More particularly, the present invention relates to apparatus and method for restoring and/or enhancing the earth's dc magnetic field, that has been degraded by time, that is degraded in a particular geographical area, that is being degraded by any man-made structure, and/or that is being degraded by an ELF (extra-low-frequency) or an rf (radio frequency) magnetic field, and for applying the restored/enhanced magnetic field into an internal portion, or into an entire being, of a human being or other living thing.

2. Description of the Related Art

Various magnetic devices have been designed, patented, and sold as healing devices. For instance, permanent magnets have been used as shoe insoles, attached to various body parts, and distributed over large areas to provide magnetic mattress pads or blankets.

While the healing power of magnetic fields might be questioned, athletes and horse trainers are convinced that permanent magnets applied to a body part relieve muscle soreness and promote healing, and many individuals believe that permanent magnets relieve their arthritic pain. Some believe that healing is a result of increased blood flow proximal to the magnet.

Permanent magnets and permanent magnet devices that are sold for magnetic therapy may apply magnetic field densities of up to 1400 gauss to skin and flesh proximal to the magnet. While, the effect of these gauss levels on DNA might be questioned, there seems to be no evidence that they do any harm.

Included among patents that teach the use of permanent magnets for healing are: Markoll, U.S. Pat. No. 5,665,049, issued Sep. 9, 1997; Guay et al., U.S. Pat. No. 5,226,185, issued Jul. 13, 1993; and Sakuma et al., U.S. Pat. No. 5,807,233, issued Sep. 15, 1998.

Lu et al., in U.S. Pat. No. 5,788,624, issued Aug. 4, 1998, teach magnetic treatment for disease in which a person's body is progressively scanned by permanent magnets that are placed on opposite sides of the body, and that subject progressive portions of the body to magnetic flux densities as high as 3,500 gauss (0.35 Tesla).

Continuing to consider the healing power of magnetic fields, in a December 2000 news report, treatment of malaria by a magnetic field was reported. Apparently, persons ill with malaria are placed in a room for a few hours wherein a magnetic field developed by Helmholtz coils is sufficiently high to spin red blood corpuscles.

With regard to healthful benefits of magnetic fields, U.S. Pat. No. 5,935,516, which issued on Aug. 10, 1999, Carl E. Baugh teaches the use of a magnetic field having a magnetic flux density of 1.0 to 5.0 gauss and a frequency of 0.5 to 30 Hertz. At least one company offers a device that uses pulsed magnetic fields. For instance, QRS America of Venice, Fla., offers a pad upon which a person may lie, and be subjected to magnetic-field therapy that is defined as, "quantron resonance therapy using pulsed electromagnetic fields operating at a range of frequencies."

While some magnetic fields, such as the earth's dc magnetic field, are known to be healthful, there is convincing evidence that ELF magnetic fields, particularly in the range of 50 and 60 Hertz frequencies, and also microwave rf magnetic fields, such as used by cell phones, are detrimental to health.

Reports by many researchers are available on the Internet from EMF-Link of Information Ventures, Inc., Philadelphia, Pa. 19102, regarding the harmful effects of ac magnetic fields, both in the ELF range and the rf range.

Tests on breast cancer cells conducted originally by Dr. Robert Liburty, and replicated in four other laboratories, show that ELF magnetic fields, such as 50 or 60 Hertz magnetic fields, in the range of 2.0 to 12.0 milligauss cancel the oncostatic effect of melatonin.

ELF magnetic fields have also been connected with an increase of almost four times in Alzheimer's disease among workers who use industrial sewing machines, as reported by E. Sobel and his associates in two articles published in Neurology Magazine.

In the October 2000 issue of "Environmental Health Perspectives" (v 108, pp. 967-972), a study by Dr. James Trosko's laboratory at Michigan State University in East Lansing, Mich. reports that ELF magnetic fields as low as 0.04 or 0.05 gauss can alter gene expression, and also act as a tumor promoter.

There have been disturbing reports concerning the deleterious effects of ELF magnetic fields on children. An increase in cancer and leukemia, of up to four times, has been reported to be occurring among children who live near power lines. Further, it has been reported that infant death syndrome occurs more frequently among children who live near power lines.

While much work has been done with regard to magnetic-field healing, and while the deleterious effects of ac magnetic field have been shown, both by statistical and laboratory evidence, very little has been done to overcome the deleterious effects of ac magnetic fields and thereby provide a more healthful environment.

However, Litovitz et al., in U.S. Pat. No. 5,544,665, issued Aug. 13, 1996, seek to overcome the harmful effects of ac magnetic fields by superimposing a "confusion" magnetic field onto an ac magnetic field.

While it is well-known that the earth's dc magnetic field is healthful and necessary for cell communication, it is also well-known that the earth's dc magnetic field is decreasing exponentially, as a function of (the mathematical number) "e" to a negative exponent that is equal to time in years, multiplied by a constant. Therefore, the earth's dc magnetic field quite likely is of a lower magnitude than that which would provide optimum health.

Further, the magnitude of the earth's dc magnetic field varies regionally, so that the earth's dc magnetic field is even further reduced in some geographical areas. Another factor is man-made structures. Man-made structures often degrade the earth's dc magnetic field in a living space. And, both the quality and effectiveness of the earth's dc magnetic field are being degraded by environmental factors, such as ELF and rf magnetic fields.

It has been reported that infant death syndrome occurs more frequently during storms of solar winds in which the earth's magnetic field is perturbated. Thus we see that infant death syndrome has been reported to be a function of both power line magnetic fields and perturbations in the earth's magnetic field. In addition, since the earth's magnetic field has "holes" in which the strength of the earth's dc magnetic field is reduced, these "holes" may be an other factor in infant death syndrome.

BRIEF SUMMARY OF THE INVENTION

Apparatus and method of the present invention, by vectorial addition of an other dc magnetic field with the earth's dc magnetic field, produce an enhanced dc magnetic field that exceeds the magnitude of the earth's dc magnetic field in its present state of time-based degradation, or that exceeds an ambient dc magnetic field that has been degraded below the magnitude of the earth's dc magnetic field by a steel structure.

In addition, or alternately, apparatus and method of the present invention provide a dc magnetic field that vectorially increases a dc ambient magnetic field, thereby at least partially obviating the detrimental effects of environmental ac magnetic fields, whether the environmental ac magnetic fields be in the range of ELF or rf magnetic fields.

More particularly, apparatus and method are provided for immersing a critical body component of a living thing, or an entire body of a living thing, into a dc magnetic field of increased magnetic intensity for extended periods of time, such as during working hours, recreation, and/or sleep, for healthful living and/or magnetic therapy.

In one basic embodiment, apparatus for providing a restored and/or enhancing dc magnetic field, includes an electrically-powered magnetic-field generator, that is attached to or built into, a structure, such as a building, a room, a bed, or an other article of furniture, but may be attached to, or built into, a portable or mobile apparatus, such as a carrel, or a vehicle.

Whether the present invention is practiced to provide a restored dc magnetic field or an enhanced dc magnetic field, the magnetic field that is to be vectorially added must be nonreversing, or unidirectional, in the living space in which the dc magnetic field is to be enhanced or restored. That is, the magnetic flux must flow in a nonreversing direction in the living space in which the magnetic flux density is to be restored or enhanced.

In another basic embodiment, apparatus for providing a restored and/or enhancing dc magnetic field to a portion of a person or living thing, includes a magnetic-field generator that may be in the form of a flexible magnetic strip or sheet, and that is worn by, or attached to a body member of, a person, or an other living thing.

Preferably, the generated dc magnetic field has a time-weighted average that exceeds 1.0 gauss, but may be as low as 0.1 gauss, and the method of the present invention comprises vectorially adding the generated dc magnetic field to the earth's dc magnetic field, at any gauss level and at any vectorial angle that results in a vectorially increased dc magnetic field, or that results in a restored dc magnetic field that has been degraded by an ac magnetic field or any other means.

A magnetic-field restored/enhanced living space, as defined herein, is any area in which a dc magnetic field is restored and/or enhanced to a height that will envelope a human or any other living thing, or a number of living things, in which a living thing normally resides for a purpose other than being in a magnetic field that has been restored/enhanced, and in which the living thing continues normal activities.

As taught herein, magnetic-field restored/enhanced living spaces may include entire floor areas, or partial floor areas, of houses, buildings, factories, rooms in houses, hospital or nursing home rooms, offices, barns, animal trailers, animal housing, animal retaining areas, hatcheries, incubators, greenhouses, and any other structure that may be used for a living space for any living thing.

Further, magnetic-field restoring/enhancing apparatus may include home and office furniture, work carrels, TV carrels, carrels for hospital and nursing home patients, and any other apparatus in which the primary use for the apparatus is other than exposure to a healthful magnetic field, and in which the primary use for the living space is continued during exposure to healthful magnetic fields.

Magnetic-field restored/enhanced living spaces may be disposed above sleeping areas of beds in homes, nursing homes, and hospitals, in bassinets, play pens, beds, and strollers for infants and children, and in vehicles for personal use, public transportation, or freight transportation.

Each type of magnetic-field-enhancing or magnetic-field-restoring apparatus includes a magnetic-field generator. A magnetic-field generator may consist of a multi-turn generator coil, permanent magnets, one or two sheets of magnetic material, electromagnets, or semi-permanent electromagnets. A semi-permanent magnet, as defined herein, is a magnet in which the core material requires periodic remagnetizing.

With regard to magnetic-field generators that consist of multiturn generator coils, as is well-known to those skilled in the art, all of the magnetic flux of a coil flows axially through a coil, flows nonreversingly, or unidirectionally, out one end of the coil, reverses directions by curving outwardly, flows outside the coil toward the opposite end of the coil, reverses directions by curving inwardly, and flows unidirectionally into an other end of the coil.

In like manner, with regard to sheets of magnetic material, as is well-known to those skilled in the art, when a permanent magnet has a single pole on each of two faces, all of the magnetic flux flows nonreversingly, or unidirectionally, from one face, reverses directions by curving outwardly, and flows outside of the permanent magnet toward the opposite face, reverses directions by curving inwardly, and flows unidirectionally into the other face.

In some embodiments, magnetic-field generators of the present invention surround, or partially surround, a living space, or surround, or partially surround, an area projected from a living space.

For instance, if a magnetic-field generator is disposed around a perimeter of a mattress, then it surrounds an area that is projected downward from a sleeping area above the mattress, and the living space is disposed above the sleeping area. Further, in magnetic-field generators for work carrels or TV carrels, if only three walls are used, and one side is left open, then the magnetic-field generator partially surrounds the magnetic-field-enhanced living space.

Magnetic-field generators disclosed herein may be used to produce magnetic poles that are disposed at any desired angle. Preferably, an angle is chosen that will provide the greatest vectorial addition to the earth's magnetic field. However, for body-worn magnetic-field generators, vertical pole orientation is preferred to keep the vectorial sum more nearly constant without regard to polar orientation of the wearer.

In a first aspect of the present invention, a method for permeating an entire living thing with a dc magnetic field that is greater than an ambient dc magnetic field comprises: generating a dc magnetic field that permeates a living space with a unidirectional dc magnetic field having a magnetic flux density that is greater than 0.1 gauss; vectorially adding the unidirectional dc magnetic field to the ambient dc magnetic field in the living space; the vectorially adding step comprises producing a dc magnetic field vector in the living space that is greater than either the unidirectional dc magnetic field or the ambient dc magnetic field; and disposing the living thing in the living space.

In a second aspect of the present invention, a method for restoring a normal dc magnetic field vector in a living space wherein earth's dc magnetic field has been degraded by vectorial addition of an ac magnetic field comprises: generating a dc magnetic field that permeates the living space with a unidirectional dc magnetic field having a magnetic flux density that is greater than 0.1 gauss; vectorially adding the unidirectional dc magnetic field to the degraded dc magnetic field; and the vectorially adding step comprises producing a dc magnetic field vector that is greater than either the unidirectional dc magnetic field or the degraded dc magnetic field, and that is equal to, or greater than, the normal dc magnetic field vector.

In a third aspect of the present invention, a method for providing an enhanced dc magnetic field above a sleeping surface comprises: generating a unidirectional dc magnetic field; the generating step comprises magnetizing a sheet of magnetic material in a manner in which one side functions substantially as a single North magnetic pole and an other side functions substantially as a single South magnetic pole; sizing the magnetized sheet to correspond to the sleeping surface; disposing the magnetized sheet proximal to the sleeping surface; and the disposing step comprises orienting the single North magnetic pole of the magnetized sheet proximal to earth's South magnetic pole.

In a fourth aspect of the present invention, a method for permeating a portion of a body member with a dc magnetic field comprises: sizing a strip of magnetic material that includes two sides and two edges that connect the sides; magnetizing the strip of magnetic material in a manner in which one of the edges functions substantially as a single North magnetic pole and an other of the edges functions substantially as a single South magnetic pole; disposing the magnetized strip around a portion of a circumference of the body member; and disposing the single North magnetic pole proximal to earth's South magnetic pole.

In a fifth aspect of the present invention, a method for providing an enhanced unidirectional dc magnetic field comprises: generating a unidirectional dc magnetic field; the generating step comprises magnetizing a sheet of magnetic material in a manner in which one side functions substantially as a single North magnetic pole and an other side functions substantially as a single South magnetic pole; disposing the North pole proximal to a South pole of earth's magnetic field; and placing the magnetized sheet onto a horizontal surface.

In a sixth aspect of the present invention, a method for providing an enhanced unidirectional dc magnetic field above a seating portion of a seat comprises: magnetizing a sheet of magnetic material in a manner in which one side functions substantially as a single North magnetic pole and an other side functions substantially as a single South magnetic pole; disposing a first portion of the magnetized material proximal to, and generally parallel to, a back portion of a seat; disposing a second portion of the magnetized material proximal to, and generally parallel to, a seating portion of the seat; and disposing a North pole of said second portion proximal to a South pole of earth's magnetic field.

A first object of the invention is to provide a biologically-enhanced dc magnetic field in a living space, for work, sleep, relaxation, and/or play, for a person's, or living thing's, entire body, by vectorially adding an other dc magnetic field with the earth's dc magnetic field to produce a dc magnetic field whose vector sum is greater than the earth's dc magnetic field.

A second object of the invention is restore a dc magnetic field, that has been degraded by an ac magnetic field, that has been degraded by a natural geological formation, or that has been degraded by a man-made structure or vehicle, by vectorially adding an other dc magnetic field with the earth's dc magnetic field, and thereby provide a restored dc magnetic field whose vector-added dc component is greater than the earth's dc magnetic field, and to provide the vector-added dc magnetic field in a living space, for work, sleep, relaxation, and/or play, for a person's, or living thing's, entire body.

A third object of the invention is to provide apparatus and method for overcoming the detrimental effects of ELF and rf magnetic fields, such as altering of gene function or promotion of cancer, by vectorial addition of an other dc magnetic field with the earth's dc magnetic field, and for applying the vectorially-added dc magnetic field to an internal body part, or to the entire body of a person.

A fourth object of the invention is to provide body-worn apparatus for vectorially-increasing the dc magnetic field in an internal body part, during normal work, sleep, relaxation, and/or play.

A fifth object of the present invention is to provide apparatus and method that provides entire-body-engulfing dc magnetic fields for use in intensive human and animal biomagnetic therapy.

BRIEF DESCRIPTION OF THE SEVERAL VIEWS OF THE DRAWINGS

FIG. 28 is a top view of a bassinet that is magnetic-field-enhancing, showing padding that spaces a baby from one or more perimetrically-disposed magnetic-field generators;

FIG. 29 is a cross-sectional side elevation of the magnetic-field-enhancing bassinet of FIG. 28, taken substantially as shown by section line 29-29 of FIG. 28, indicating alternate magnetic-field generator locations/designs, and showing a battery installed beneath a living surface;

FIG. 30 is a side elevation of a prior-art permanent magnet of domino shape, showing the flow of magnetic flux around ends thereof;

FIG. 31 is an end elevation of two, spaced-apart permanent magnets with North poles disposed upwardly, illustrating that the earth's magnetic field is enhanced both inside and outside the magnets, and that the earth's magnetic field is enhanced substantially equally above and below the magnets;

FIG. 32 is an isometric drawing of a parallel-bar magnetic-field generator, showing a magnetic-field-enhanced living space in phantom lines;

FIG. 33 is an isometric drawing of a closed-ring magnetic-field generator;

FIG. 34 is a side elevation of a magnetic-field-enhancing bassinet, playpen, or bed in which a magnetic-field generator, in the form of a sheet of magnetized material, is disposed under a mattress;

FIG. 35 is an end elevation of the magnetic-field-enhancing bassinet, playpen, or bed of FIG. 34;

FIG. 35A is a partial end elevation of the magnetic-field-enhancing bassinet, playpen, or bed of FIGS. 34 and 35, showing the magnetic-field generator angled near edges thereof to focus the enhancing magnetic field;

FIG. 35B is a partial end elevation of the magnetic-field-enhancing bassinet, playpen, or bed of FIGS. 34 and 35, showing the magnetic-field generator angled near edges and ends thereof to focus the enhancing magnetic field;

FIG. 35C is a partial end elevation of a magnetic-field-enhancing mattress that uses a magnetized pad for the magnetic-field generator;

FIG. 35D is a partial end elevation of a magnetic-field-enhancing mattress that uses a magnetized pad for the magnetic-field generator, and that includes a longitudinally-disposed strip of magnetized sheet along each edge to increase the strength of the magnetic field;

FIG. 36 is a side elevation of a child sitting in a magnetic-field-enhancing car seat that is strapped in a vehicle, showing the magnetic-field generator in phantom lines, and also showing, in phantom lines, a sleeping position of the child's head, to illustrate the fact that the enhancing magnetic-field-enhancing apparatus envelops the child's head, whether the child is awake or asleep;

FIG. 37 is a side elevation of a magnetic-field-enhancing apparatus in the form of a magnetic-field-enhancing baseball cap, or Magcap;

FIG. 37A is a partial and enlarged cross-section of the baseball cap of FIG. 37, taken substantially as shown by section-line 37A-37A of FIG. 37, showing the crown-shaped magnetic-field generator pad thereof;

FIG. 38 is a perspective drawing of a person wearing a magnetic-field-enhancing apparatus in the form of a magnetic-field-enhanced headband, Magband;

DETAILED DESCRIPTION OF THE INVENTION

Before describing various embodiments of the present invention, it is important to set forth principles of operation. Thus, a basic discussion of the earth's dc magnetic field, algebraic and trigonometric vector addition of ac and dc magnetic fields, and magnetic reluctance of various materials, including the human body, is in order.

Figure 1:
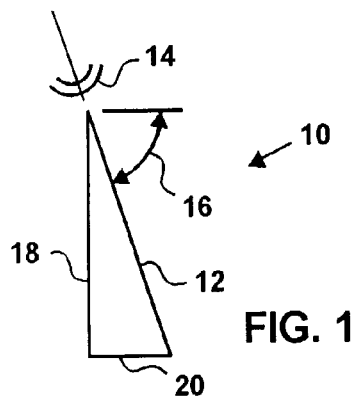
FIG. 1 is a vector diagram showing declination of the North pole in the Northern hemisphere and both horizontal and vertical components thereof.

Referring now to FIG. 1, in a vector diagram 10, a dc vector 12 of earth's dc magnetic field 14 points not only to the North, but also points downwardly at an angle 16, because the North pole is downward from horizontal in the Northern hemisphere. Thus, the dc vector 12 includes a vertical component 18 and a horizontal component 20. In the vicinity of Chicago, Ill., the angle 16 is 72.0 degrees. And, in most parts of the earth, the magnitude of the earth's dc magnetic field 14 is about 0.5 gauss.

Therefore, the vertical component 18 of the dc vector 12 is only slightly less than the earth's dc magnetic field 14, since it is equal to 0.5 gauss multiplied by the cosine of 72.0 degrees. However, the horizontal component 20 is only 0.16 gauss, because it is equal to 0.5 gauss multiplied by the sine of 72.0 degrees.

Figure 2:
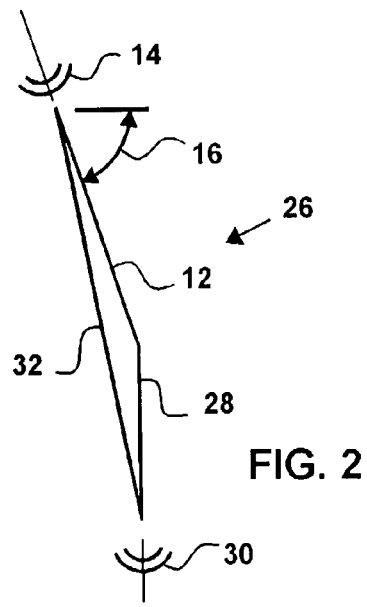
FIG. 2 is a vector diagram of an other dc magnetic field being vectorially added to the earth's dc magnetic field.

Referring now to FIG. 2, in a vector diagram 26, the dc vector 12 of the earth's dc magnetic field 14 is depending downwardly at the angle 16 which is 72.0 degrees. And, an other dc vector 28 of an other dc magnetic field 30 has been vectorially added to provide a resultant dc vector 32 that is greater than the dc vector 12 of the earth's dc magnetic field 14.

Figure 3:
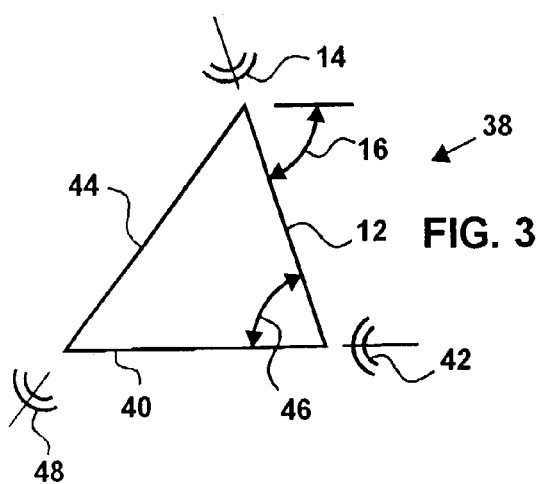
FIG. 3 is a vector diagram of still an other dc magnetic field being vectorially added to the earth's dc magnetic field wherein an angle between the two dc magnetic fields is greater than shown in FIG. 2.

Referring now to FIG. 3, in a vector diagram 38, the dc vector 12 of the earth's dc magnetic field 14 is depending downwardly at the angle 16. And, an other dc vector 40 of an other dc magnetic field 42 has been vectorially added to provide a resultant dc vector 44 that is greater than the dc vector 12 of the earth's dc magnetic field 14.

Summarizing the principles taught in FIGS. 2 and 3, and referring again to FIG. 3, in the present invention, the other dc vector 40 of the other dc magnetic field 42 is vectorially combined, at any angle 46, with the dc vector 12 of the earth's dc magnetic field 14, to produce a resultant dc magnetic field 48 whose resultant dc vector 44 is greater than the dc vector 12 of the earth's dc magnetic field 14.

Figure 4:
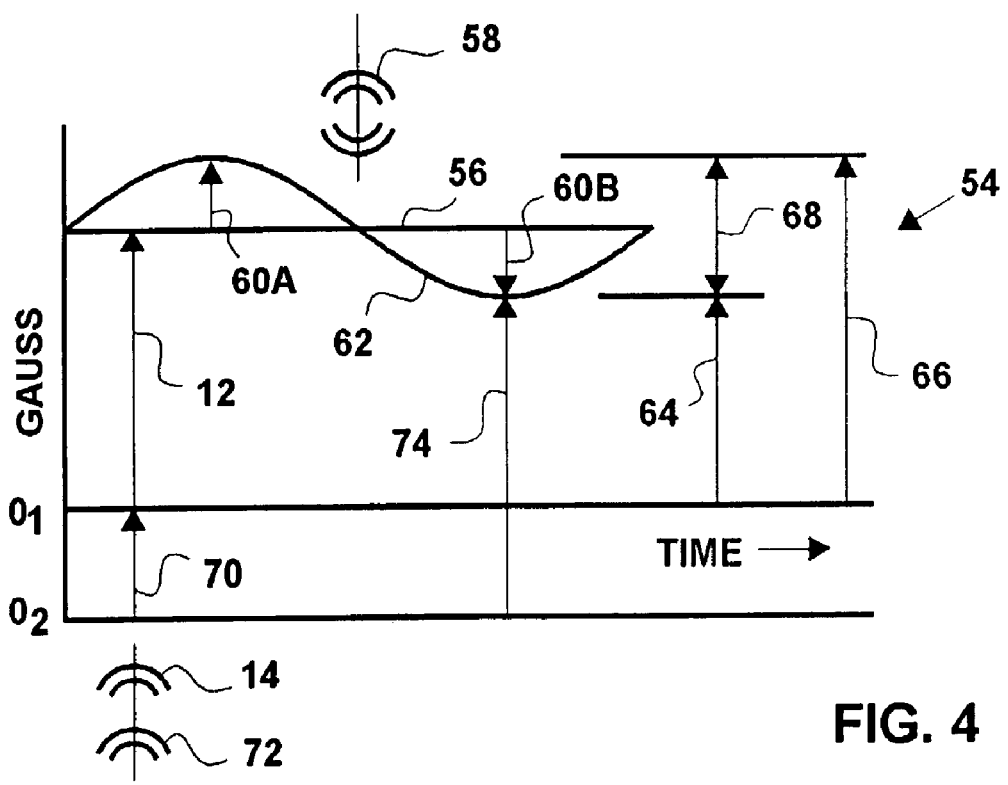
FIG. 4 is a graph of gauss vs. time, showing an ac magnetic field has degraded the earth's dc magnetic field, and showing how an other dc magnetic field, algebraically added to the earth's dc magnetic field, not only restores a normal minimum dc magnetic field, but also enhances the dc magnetic field.

Referring now to FIG. 4, a graph 54 of gauss vs. time shows the dc vector 12 of the earth's dc magnetic field 14 oriented upwardly as graphs ordinarily show increasing magnitude. Since the earth's dc magnetic field 14 is a constant, the dc vector 12 of the earth's dc magnetic field 14 is also represented as a horizontal line 56.

An ac magnetic field 58 has been imposed onto the earth's dc magnetic field 14. Cyclically-variable vectors 60A and 60B of the ac magnetic field 58 are shown in their respective locations along a sinusoidal curve 62. The sinusoidal curve 62 shows the direction and vector magnitudes of the ac magnetic field 58 vs. time.

For simplicity, the magnetic fields 14 and 58 are assumed to be in a plane of the paper, so the dc vector 12, and either one of the cyclically-variable vectors, 60A or 60B, can be added algebraically, rather than trigonometrically. Algebraic addition of the dc vector 12 of the earth's dc magnetic field 14 with the cyclically-variable vector 60B of the ac magnetic field 58 results in a minimum flux-density vector 64 that occurs cyclically. And, algebraic addition of the dc vector 12 and the cyclically-variable vector 60B results in the dc vector 12 of the earth's dc magnetic field 14 being increased cyclically to a maximum flux density-vector 66 that occurs cyclically. A vector 68 represents the total cyclic variation in the dc vector 12 that is caused by the ac magnetic field 58.

Continuing to refer to FIG. 4, if a vector 70 of an other dc magnetic field 72 is algebraically added to the dc vector 12 of the earth's dc magnetic field 14, the zero position of the graph 54 shifts from $0^1$ to $0^2$, and the minimum flux-density vector 64 is increased to a new minimum flux-density vector 74. If the vector 70 of the other dc magnetic field 72 is greater than the cyclically-variable vector 60B, then the new minimum flux-density vector 74 is greater than the dc vector 12 of the earth's dc magnetic field 14, and a normal dc magnetic field is restored.

Therefore, in the present invention, use of an other dc magnetic field, such as the dc magnetic field 72 is used to restore the magnitude of the earth's dc magnetic field 14, thereby promoting effective cell communication, when the earth's dc magnetic field 14 has been degraded by an ac magnetic field, such as the ac magnetic field 58.

Figure 6:
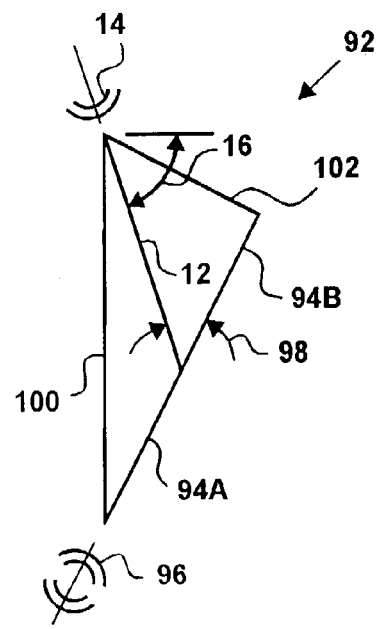
FIG. 6 is a vector diagram showing that opposite-pole vectors of an ac magnetic field degrade the earth's dc magnetic field.
Figure 7:
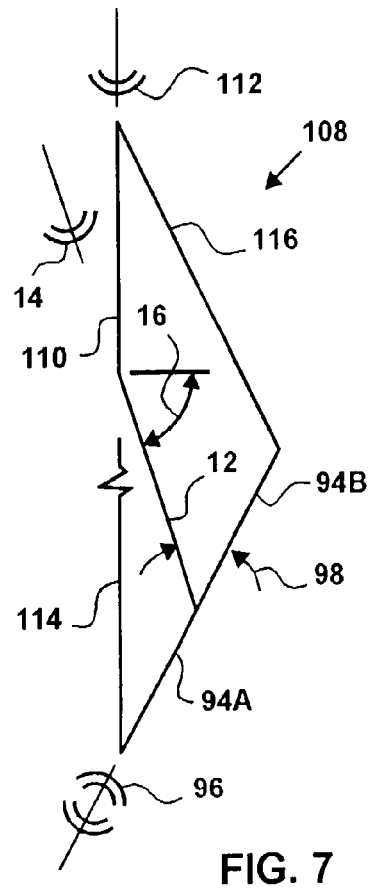
FIG. 7 is a vector diagram showing that a normal dc magnetic field, that has been degraded as shown in FIG. 6, not only has been restored, but also has been enhanced, by an other dc magnetic field.

While the earth's dc magnetic field 14, the ac magnetic field 58, and the other dc magnetic field 72 have been illustrated in FIG. 4 in vectorial alignment, so that the magnetic fields 14, 58, and 72 can be added algebraically, in most situations, practicing the invention will require trigonometric addition as will be taught in conjunction with FIGS. 6 and 7. That is, in most instances an environmental ac magnetic field will not be vectorially aligned with the earth's dc magnetic field 14, and preferably, a vectorial orientation of the other dc magnetic field is chosen to best restore a normal dc magnetic field.

Figure 5:
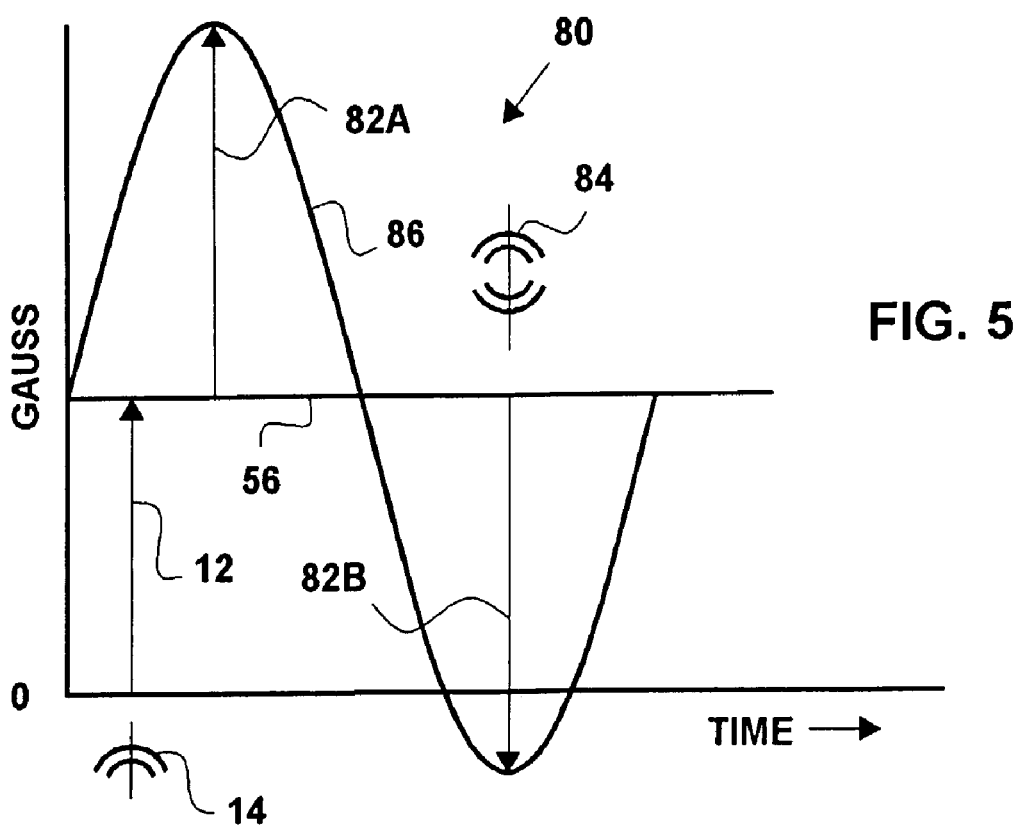
FIG. 5 is a graph of gauss vs. time, showing that an ac magnetic field, that is larger than the earth's dc magnetic field, obliterates the normal dc magnetic field of the earth.

Referring now to FIG. 5, a graph 80 of gauss vs. time shows the dc vector 12 of the earth's dc magnetic field 14 as the horizontal line 56. Cyclically-variable vectors 82A and 82B of an ac magnetic field 84 are shown along their respective positions along a sinusoidal curve 86. Since, as shown, the cyclically-variable vectors 82A and 82B are greater than the dc vector 12, the dc vector 12 of the earth's dc magnetic field 14 is destroyed by the cyclically-variable vector 82B of the ac magnetic field 84. However, in like manner as taught in conjunction with FIG. 4, if an other dc magnetic field, of sufficient flux density, were added to the dc vector 12, a minimum flux density, equal to the earth's dc magnetic field 14, would be restored.

Referring now to FIG. 6, a vector diagram 92 shows trigonometric addition of the dc vector 12 of the earth's dc magnetic field 14 and cyclically-variable vectors 94A and 94B of an ac magnetic field 96. The earth's North magnetic pole depends downwardly at the angle 16, which is 72.0 degrees in the vicinity of Chicago, Ill. The magnetic fields 14 and 96 are at an angle 98 that is 45 degrees.

Trigonometric addition of the dc vector 12 and the cyclically-variable vector 94A results in a cyclically-maximum flux-density vector 100. More importantly, trigonometric addition of the dc vector 12 and the cyclically-variable vector 94B results in a minimum dc flux-density vector 102 that is smaller than the dc vector 12 of the earth's dc magnetic field 14. Therefore, the earth's dc magnetic field 14 has been degraded by the ac magnetic field 96.

Referring now to FIG. 7, a vector diagram 108 adds a vector 110 of an other dc magnetic field 112 to the vector diagram 92 of FIG. 6. That is, the vector diagram 108 shows trigonometric addition of the dc vector 12 of the earth's dc magnetic field 14, the vector 110 of the other dc magnetic field 112, and the cyclically-variable vectors 94A and 94B of the ac magnetic field 96. The earth's North magnetic pole depends downwardly at the angle 16, which is 72.0 degrees, and the ac magnetic field 96 is at the angle 98, which is 45.0 degrees, to the earth's dc magnetic field 14.

Trigonometric addition of the dc vector 12, the vector 110, and the cyclically-variable vector 94A results in a cyclically-maximum flux-density vector 114 which is shown as a broken line, since a portion would overlap the vector 110. More importantly, trigonometric addition of the dc vector 12, the vector 110, and the cyclically-variable vector 94B results in a minimum dc flux-density vector 116 that is larger than the dc vector 12 of the earth's dc magnetic field 14.

Therefore, the dc vector 12 of the earth's dc magnetic field 14, that had been degraded by the ac magnetic field 96 to be equal to the minimum dc flux-density vector 102 of FIG. 6, which is less than the dc vector 12 of the earth's dc magnetic field 14, has been restored by the other dc magnetic field 112 as shown by the minimum dc flux density vector 116 of FIG. 7. Further, the other dc magnetic field 112 not only has restored the dc vector 12 of the earth's dc magnetic field 14, it also has enhanced the earth's dc magnetic field 14, because the minimum dc flux-density vector 116 is larger than the dc vector 12.

In the present invention, instead of using magnetic field densities of up to 1,400 gauss, as taught by some for use in magnetic therapy, the present invention uses magnetic field densities in the range of about 0.1 to 5.0 gauss. But, can magnetic flux densities as low as taught herein even penetrate human flesh?

Resistance to flow of magnetic flux through materials is called, "reluctance" or "magnetic reluctance." For a vacuum, air, and most nonmagnetic materials, magnetic reluctance is equal to, or very nearly equal to, 1.0 gauss.

Magnetic reluctance of iron and steel varies, with composition, hardness, and the degree of magnetization, from about 0.016 to 0.00025, so curves, rather than tables, are used to determine values of magnetic reluctance. Generally speaking, the magnetic reluctance for most steels is on the order one one-thousandths that of air and non-magnetic materials.

It is difficult to find technical information on the magnetic reluctance of the human body. Fortunately, it is easy to determine that the reluctance of the human body is the same as, or very nearly the same as, air. Tests to determine the reluctance of the human body can be made with an instrument as simple as a camping compass, or with a Hall-effect gaussmeter.

As taught in conjunction with FIG. 1, the horizontal component 20 of the earth's dc magnetic field 14 is about 0.16 gauss. This means that a compass needle is positioned by a magnetic field of only 0.16 gauss. Can a magnetic field density of 0.16 gauss position a compass needle through a body of a human being? If so, then the magnetic reluctance of the human body must be nearly the same as air.

If two individuals are positioned back to back with one facing North and the other facing South, with about three inches between their backs, and a case of a compass, that is off to one side of the two individuals, is rotated rapidly about 90 degrees, the compass needle will be pointing East or West. If then, the compass is positioned rapidly between the backs of the two individuals, the compass needle will find North as quickly as it does in air.

If the magnetic reluctance of the human body were, to any extent, greater than that of air, the two individuals would shield the compass needle from the earth's dc magnetic field, and the compass needle could not find North. And yet, reproducing this test will show that a compass needle will point to the North pole directly through one of the individuals.

In a similar test, if a person stands with his back toward the North pole, and moves a compass from the left of himself, past his front, and to the right of himself, he will see that the compass needle continuously points directly toward the North. If the magnetic reluctance of the human body were, to any extent, greater than that of air, then the compass needle would show the magnetic flux detouring around him, and then closing in around him to continue a path of least reluctance.

Magnetic field restorers and magnetic field generators of the present invention include embodiments in which permanent magnets are worn on the head, body, or some other body part of an individual. But is it possible to develop a magnetic flux density in a body-worn magnet that will penetrate the human body with a magnetic flux density of 0.1 gauss, or greater? Or, would a body-worn magnet, that would produce a magnetic field somewhere between 0.1 and 5.0 gauss be too heavy to wear on the body?

Figure 8:
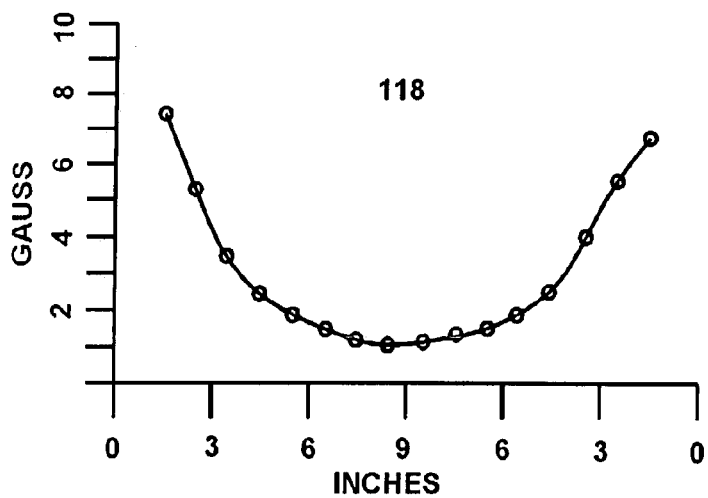
FIG. 8 is a graph of gauss vs. distance for a magnetic field centered between two rectangular pieces of magnetized flexible sheet.

Referring now to FIG. 8, a graph 118 shows magnetic flux densities, in gauss vs. distance in inches, from respective ones of faces of two sheets of flexible magnetic material, not shown. The two sheets of magnetic material for this test were 8.250 inches (21.0 cm) wide, 6.375 inches (16.2 cm) high, and 0.060 inches (1.52 mm) thick, weighed 6.7 ounces (190.3 grams) each, and were magnetized with only a single magnetic pole on each side.

In the test of FIG. 8, the two sheets of flexible magnetic material were spaced apart 18 inches (45.8 cm), and air was the medium between the two sheets of magnetic material. As shown by the graph 118 of FIG. 8, the two sheets of magnetic material would produce a magnetic-field density of 1.0 gauss in the innermost part of an object, such as a human body, that is 18.0 inches (45.8 cm) thick.

It has been proven previously that magnetic fields penetrate the human body as easily as they do air. Therefore, the test of FIG. 8 proves that body-worn magnets, light enough to be carried, can produce a magnetic field that can penetrate a human body. More especially, the test of FIG. 8 shows that two sheets of flexible magnetic material that weigh only 6.7 ounces (190.3 grams) each can produce a magnetic field in the innermost organ of a person, who is 18.0 inches (45.7 cm) thick, an enhancing magnetic field whose magnitude is twice that of the earth's dc magnetic field and ten times the minimum gauss level taught herein.

Quite a number of patents have been granted for use in magnetic therapy on the basis of unique distribution of magnetic poles on surfaces of flexible magnetic sheets. Among these are Spiegler, U.S. Pat. No. 6,416,458 which issued on Jul. 9, 2002; and Brisoni et al., U.S. Pat. No. 6,267,719 which issued on Jul. 31, 2001.

In addition, two patents, pertaining to therapeutic use of magnetic fields, have been granted in which flexible magnetic material includes only a single pole on each side. Flamant et al., in U.S. Pat. No. 6,126,588 which issued on Oct. 3, 2000, teach a flexible magnetic material that will drape to follow contours of a human body. And, Gardner et al., in U.S. Pat. No. 5,621,369, teach a flexible magnet that includes a pattern of ridges that are designed to produce a dispersed magnetic field.

While flexible magnets with alternating, or patterned, magnetic poles on each side have produced a confusion of magnetic fields that penetrate the body to superficial depths, Flamant et al. have oriented the South magnetic pole toward the body member needing therapy. In contrast, Griffin et al. in U.S. Pat. No. 5,587,956 teaches juxtaposing one polarity of a magnetic pad against a body member, and at a later time, reversing the magnetic pad.

In contrast, in the present invention, magnetic poles are oriented to enhance the earth's dc magnetic field, to restore an ambient dc magnetic field that has been degraded by a steel structure, to restore a dc magnetic field that has been degraded by an ac magnetic field, or to provide magnetic-field penetration completely through a body, or a body member, by providing opposite magnetic poles on opposite sides of the body or body member.

The magnetic pole at the geographical North Pole is not magnetically a North pole, but instead it is magnetically a South pole. Therefore, enhancing and/or restoring the earth's dc magnetic field is accomplished by orienting a North magnetic pole of a magnetic-field generator toward the (supposedly) North magnetic pole.

But, since the (supposedly) North magnetic pole is oriented downwardly at 72.0 degrees from North in the vicinity of Chicago, Ill., at that geographical location, vertical orientation of the magnetic poles of the enhancing magnetic field is almost ideal, with the North magnetic pole of the magnetic-field generator being disposed downwardly. However, magnetic-field enhancing or magnetic-field restoring as taught herein can be accomplished by vector addition at any angle that results in restoring or enhancing the earth's dc magnetic field.

Figure 9:
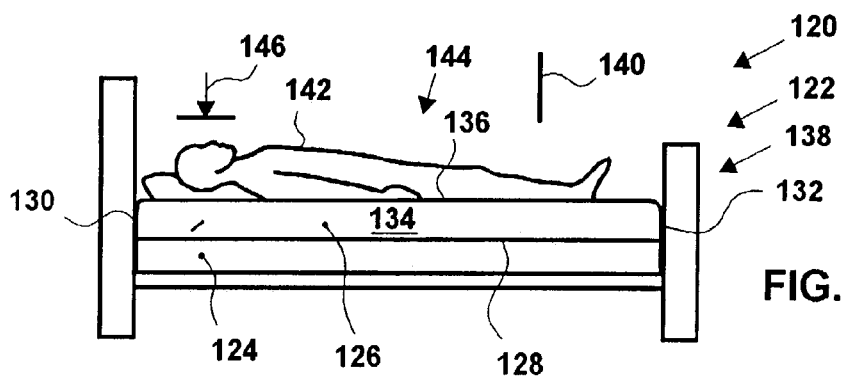
FIG. 9 is a side elevation of a magnetic-field-enhancing bed with a magnetic-field generator both horizontally and circumferentially disposed with respect to an upper and a lower sleep unit.

Referring now to FIG. 9, a magnetic-field-enhancing bed or magnetic-field enhancing apparatus 120 includes a bed, or bed structure, or furniture structure 122, a box spring or lower sleep unit 124, a mattress, or upper sleep unit 126, and a magnetic-field generator 128 that is disposed between the lower sleep unit 124 and the upper sleep unit 126, and that is shown as a thicker line. The mattress 126 includes a head edge 130, a foot edge 132, and a pair of side edges 134 that all depend downwardly from a top surface, or sleeping surface 136, and that form a perimeter 138 around the mattress 126. The magnetic-field generator 128 produces exclusively North and South magnetic poles as shown, and a resultant dc magnetic field that is oriented generally along flux lines 140.

The magnetic-field generator 128 is designed to produce a magnetic field with a magnitude of about 0.5 to 5.0 gauss that passes through a person, or body of a human, 142. More particularly, the magnetic-field generator 128 is designed to enhance or restore the earth's dc magnetic field in a living space 144 that extends upwardly for a height 146 from the top surface 136 that is sufficient to engulf the body of the person 142. Obviously, the edges 130, 132, and 134 define a length, not numbered, and a width, not numbered, of the living space 144.

Figure 10:
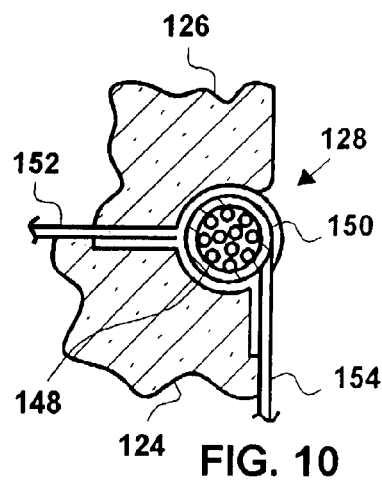
FIG. 10 is a partial cross section of the magnetic-field generator 138 of FIG. 9.

Referring now to FIG. 10, the magnetic-field generator 128 is shown disposed between the lower sleep unit 124 and the upper sleep unit 126 of FIG. 9. The magnetic-field generator 128 includes a multi-turn generator coil 148, a coil sheath 150, a web 152 for disposing between the lower sleep unit 124 and the upper sleep unit 126, and a skirt 154.

Figure 11:
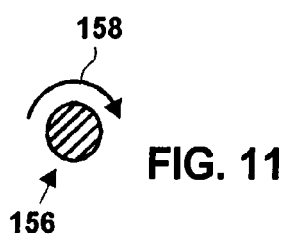
FIG. 11 is a cross-section of a wire carrying a current that is flowing downward into the paper, showing a magnetic field that is developed thereby.

Referring now to FIG. 11, a wire 156 is shown in cross-section. If a current is flowing downward through the wire 156 into the paper, the current flow through the wire 156 develops magnetic flux in the direction shown by an arrow 158. With the thumb of the right hand in the direction of current flow, the direction of the magnetic flux around the wire is in the direction of fingers of the right hand.

Figure 12:
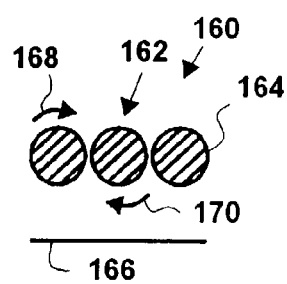
FIG. 12 is a cross-section of a multi-turn generator coil with a longitudinal axis disposed below the cross-sectioned coils, and with current flowing downward into the paper, showing magnetic flux and magnetic poles developed thereby.

Referring now to FIG. 12, a multi-turn generator coil 160 is shown in cross-section, and includes a plurality of turns 162 of wire 164 that are wound around an axis 166. If current is flowing downwardly through the turns 162 of wire 164 into the paper, magnetic flux flows generally as shown by an arrow 168, and develops North and South magnetic poles as shown, but some magnetic flux flows between coils, as shown by an arrow 170. With fingers of the right hand pointing in the direction of current flow through the turns 162 of wire 164, the thumb points toward the North pole.

Referring again to FIG. 9, in like manner to the multiturn generator coil 160 of FIG. 12, magnetic flux flows from one pole of the magnetic-field generator 128 along the flux lines 140, and nonreversibly, or unidirectionally, through the living space 144, and returns to the opposite pole of the magnetic-field generator 128.

Figure 13:
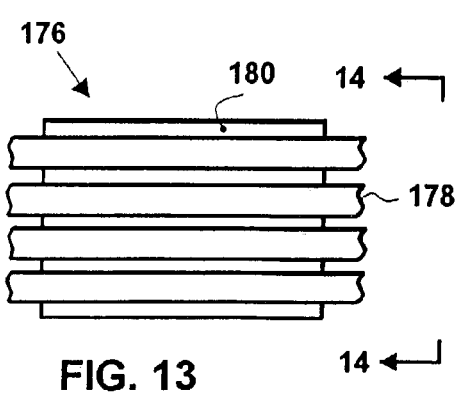
FIG. 13 is a partial plan view of an generator-coil wrap in which strips of conductive material are bonded to a non-conductive backing, which may be used to construct a magnetic-field generator for a bed, which may be used inside a room before application of Sheetrock®, or any other type of wall board, or which may be used for wrap around a building, either under or over sheeting, for clarity showing the strips extending from ends of the nonconductive backing.
Figure 14:
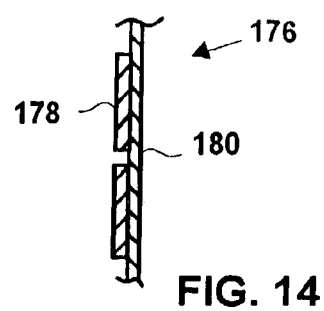
FIG. 14 is an enlarged partial view of the coil wrap of FIG. 13 taken substantially as shown by view line 14-14 of FIG. 13.

Referring now to FIG. 13, and FIG. 14 that is an enlarged cross-section taken substantially as shown by section line 14-14 of FIG. 13, a coil wrap 176 includes a plurality of strips 178 of conductive material that are spaced apart, and bonded to a nonconductive backing 180. The coil wrap 176 can be used in place of plastic wrap that is often used over sheeting in building construction, it can be used under Sheetrock®, or it can be used for making smaller coils.

Figure 15:
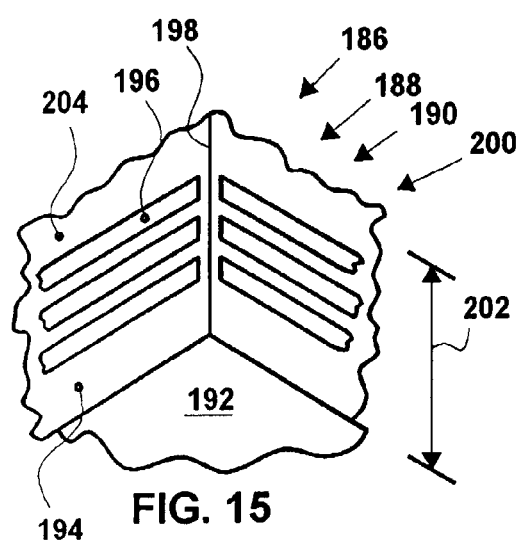
FIG. 15 is a partial perspective view in which strips of conductive material are wallpapered inside a room of an existing building which, when connected in series, provide a magnetic-field generator.

Referring now to FIG. 15, magnetic-field-enhancing apparatus or a magnetic-field enhancing room 186 includes a room or room structure 188, and a magnetic-field generator or multi-turn generator coil 190. The room 186 includes a floor 192 and interior wall surfaces 194.

Strips 196 of conductive material are wallpapered onto the interior wall surfaces 194, and are continuous around corners, except for one corner 198. When the strips 196 are connected with jumpers, not shown, the magnetic-field generator 190 is formed, thereby providing the magnetic-field enhancing room 186.

If the magnetic-field enhancing room 186 is to be used primarily for persons who will be sitting or sleeping, a magnetic-field-enhanced living space 200 does not necessarily need to extend to a height 202 that is more than 1.5 meters (5.0 feet) above the floor 204. And, since the magnetic-field enhanced living space 200 will extend both above and below the magnetic-field generator 190, the magnetic-field generator 190 does not need to be as long as the height 202.

In like manner, a living space in many building does not necessarily need to extend up to a ceiling of the building, a magnetic-field generator thereof does not necessarily need to extend down to a floor, and the magnetic-field generator does not necessarily need to extend upwardly to a height of a magnetic-field-enhanced living space.

Figure 16:
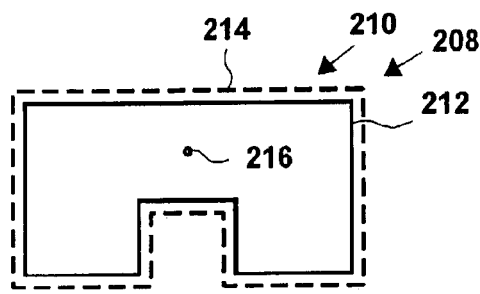
FIG. 16 is a schematic top view of a magnetic-field-enhancing building, showing a magnetic-field generator that is perimetrically disposed, as symbolized by a dash line.

Referring now to FIG. 16, a magnetic-field-enhancing apparatus or a magnetic-field enhancing building 208 includes a building or a building structure 210 with a structural perimeter 212, and a magnetic-field generator or multi-turn generator coil 214 that is symbolized by dash lines, that is applied perimetrically, and that produces poles along a vertical axis 216.

Figure 17:
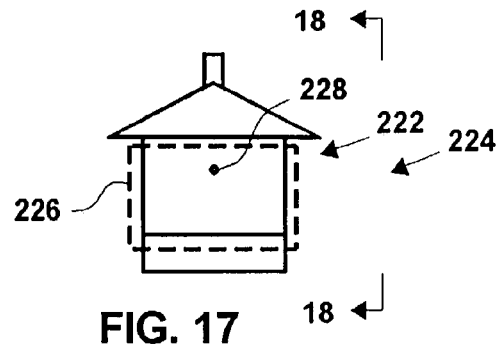
FIG. 17 is an end elevation of a magnetic-field-enhancing building in which a magnetic-field generator extends under the floor, up a side wall, across a ceiling, and down the other side wall.

Referring now to FIG. 17, an end elevation of a magnetic-field enhancing apparatus or a magnetic-field-enhancing building 222 is shown. The magnetic-field-enhancing building 222 includes a building or a building structure 224, and a magnetic-field generator or multi-turn generator coil 226 that is symbolized by a dash line. A magnetic field is produced whose poles are disposed along an axis 228.

Figure 18:
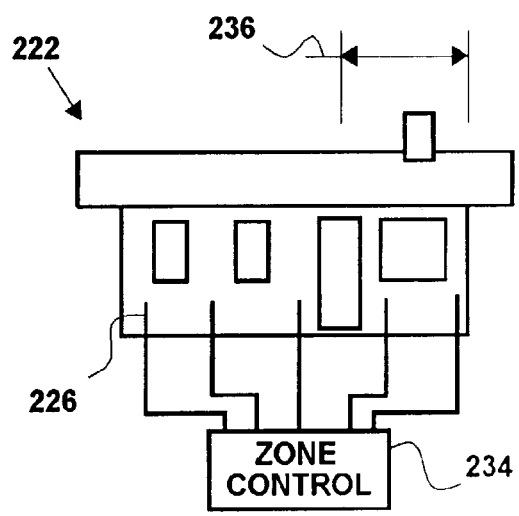
FIG. 18 is a front elevation of the magnetic-field-enhancing building of FIG. 17, taken substantially as shown by view line 18-18 of FIG. 17, showing a plurality of individual-zone generators, with a zone control shown as a block diagram.

In FIG. 18, the magnetic-field-enhancing building 222 of FIG. 17 is taken substantially as shown by view-line 18-18 of FIG. 17. The magnetic-field-enhancing building 222 includes a plurality of the generator coils 226 of FIG. 17 that are connected to a zone control 234 of FIG. 18. The zone control 234 may be programmed to apply power to selected ones of the generator coils 226, thereby magnetic-field enhancing selected ones of zones, such as a zone 236 of the building 222, in accordance with a selected use of the building 222 during a selected portion of a day.

Figure 19:
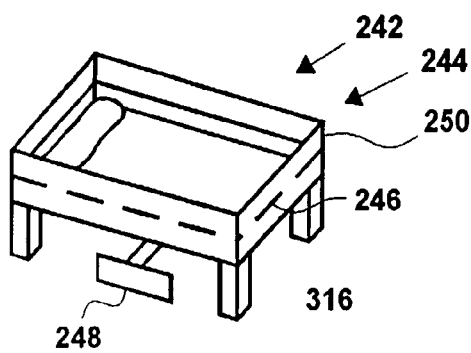
FIG. 19 is a perspective view of a magnetic-field-enhancing hospital bed with a magnetic-field-enhancing structure surrounding a hospital bed, with a magnetic-field generator symbolized by dash lines, and a mechanism to raise and lower the magnetic-field-enhancing structure.

Referring now to FIG. 19, a magnetic-field-enhancing apparatus or a magnetic-field-enhancing hospital bed 242 includes a bed or a bed structure 244, a magnetic-field generator 246 that is disposed perimetrically around the bed 242, and a lifting mechanism 248 for raising and lowering both the magnetic-field generator 246 and a surround structure 250. The magnetic-field generator 246 is disposed both horizontally and perimetrically in the surround structure 250.

The surround structure 250 serves as a bed rail when raised, whether or not a voltage is applied to the magnetic-field generator 246, and the lifting mechanism 248 lowers the surround structure 250 to provide easy entrance onto, and exit from, the bed 242.

Figure 20:
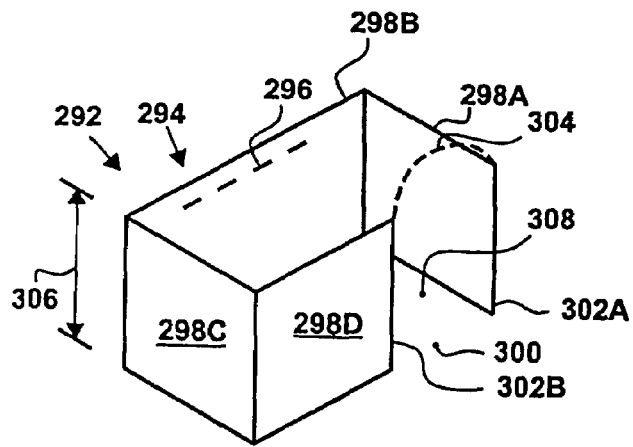
FIG. 20 is a perspective view of a magnetic-field-enhancing carrel which can be shaped to substantially enclose a work or sleep area, whose height is sufficient to provide a beneficial magnetic field for sitting or sleeping, and which can be moved through doors, showing coil jumpers as a dash line.

Referring now to FIG. 20, a magnetic-field-enhancing apparatus or a magnetic-field-enhancing carrel 292 includes a foldable carrel or a carrel structure 294 and a magnetic-field generator 296 that is symbolized by a dash line. The carrel structure 294 includes foldably-hinged panels 298A, 298B, 298C, and 298D. A portion of the magnetic-field generator 296 is disposed in each of the panels 298A-298D. The foldable carrel 294 may be shaped to substantially enclose, except for an opening 300 between ends 302A and 302B, a work space or a sleep area, or any other area in which a beneficial magnetic field is desired. A bundled-conductor jumper 304 connects portions of the magnetic field generator that are disposed in the panels 298A-298D.

The magnetic-field-enhancing carrel 292 has a height 306 that preferably is short enough to be moved through doors, not shown, and the magnetic-field generator 296 is positioned to provide a beneficial dc magnetic field in a living space 308 for sitting or sleeping.

Figure 21:
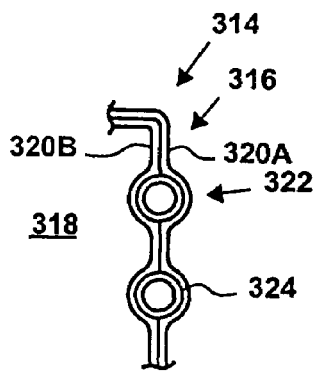
FIG. 21 is a partial elevation, in cross-section, of a magnetic-field-enhancing air mattress.

Referring now to FIG. 21, a magnetic-field-enhancing apparatus or a magnetic-field-enhancing mattress 314 includes a mattress or a mattress structure 316. The mattress 314 may be of the type wherein water is used in a cavity 318 to provide support, or which may be of the type in which air is used. The mattress 314 includes riser portions 320A and 320B. The riser portions 320A and 320B are welded together with a magnetic-field generator 322 that is made of a plurality of wires 324, and that is disposed between the riser portions, 320A and 320B.

Figure 22:
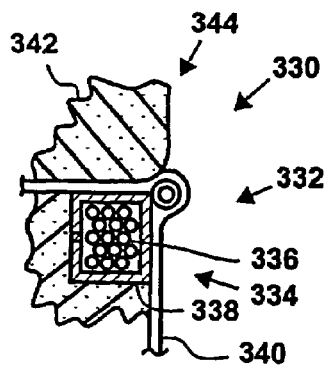
FIG. 22 is a partial elevation, in cross-section, of a magnetic-field-enhancing lower sleep unit, or box spring in which the magnetic-field generator thereof is in the form of a bundled-loop coil.

Referring now to FIG. 22, a magnetic-field-enhancing apparatus or a magnetic-field-enhancing bed 330 includes a box spring or lower sleep unit 332, and a magnetic-field generator 334. The magnetic-field generator 334 includes bundled and continuously looped wire 336 and a bundling conduit 338.

The box spring 332 includes a cloth cover 340 that encloses the magnetic-field generator 334. When the magnetic-field generator 334 is disposed under a mattress, or upper sleep unit, 342, the magnetic-field-enhancing apparatus 330 and the upper sleep unit 342 cooperate to provide a magnetic-field-enhancing bed 344. Alternately, not shown, the magnetic-field generator 334 may be made as an integral part of the upper sleep unit 342.

Figure 23:
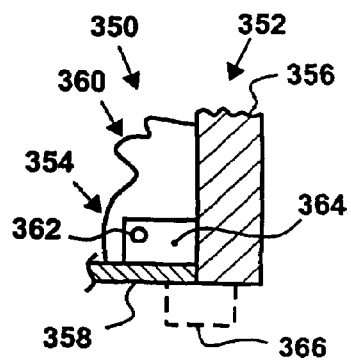
FIG. 23 is a partial elevation, in cross-section, of a magnetic-field-enhancing water bed in which the magnetic-field generator, which is in the form of a bundled-loop coil, is shown in alternate locations.

Referring now to FIG. 23, a magnetic-field-enhancing apparatus or a magnetic-field-enhancing water bed 350 includes a water bed or a water bed structure 352, and a magnetic-field generator 354. The water bed 350 includes rails 356, a bottom board 358, and a water-bed mattress 360. The magnetic-field generator 354 includes continuously-looped wire 362 with bundled turns that are disposed in a conduit 364. Alternately, the magnetic-field generator 354 may be disposed under the water bed 350 as shown by a dash line 366.

Figure 24:
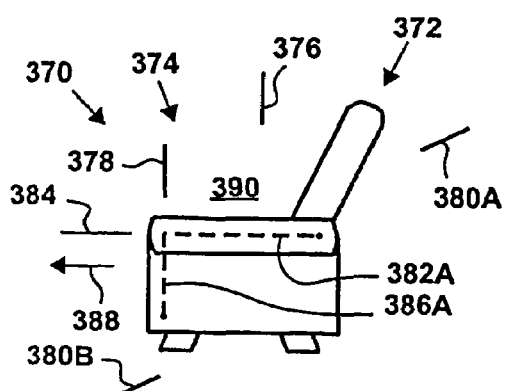
FIG. 24 is an end elevation of a magnetic-field-enhancing seating furniture, showing bundled conductors that form a two-axis magnetic-field generator.

Referring now to FIG. 24, a magnetic-field-enhancing apparatus or magnetic-field-enhancing seating furniture 370 includes seating furniture or seating furniture structure 372, and a magnetic-field generator or two-axis generator 374. The two-axis generator 374 produces a magnetic field that is disposed along two axes, one axis with poles along a vertical axis 376, and an other axis with poles along a horizontal axis 378, thereby producing a magnetic field that is distributed upward and backward, forward and downward, and therebetween, as shown by lines 380A and 380B.

The magnetic-field generator 374 includes a horizontal coil portion 382A that is disposed along a horizontal plane 384, thereby producing poles along the vertical axis 376, and a vertical coil portion 386A that is disposed along a vertical plane 388, thereby producing poles along the horizontal axis 378, and thereby producing a magnetic-field-enhanced living space 390 that is sufficient to engulf a human, not shown, seated in the magnetic-field-enhancing seating furniture 370.

Figure 25:
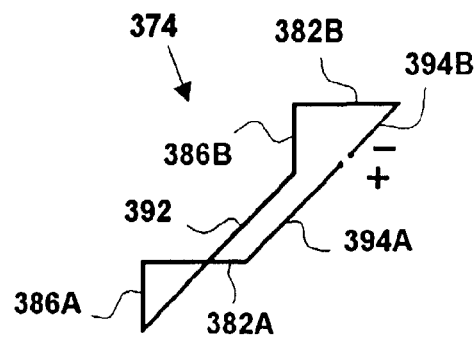
FIG. 25 is a perspective and symbolic view of a magnetic-field generator for the magnetic-field-enhancing seating furniture of FIG. 24, illustrating construction of the two-axis magnetic-field generator.

Referring now to FIGS. 24 and 25, but more particularly to FIG. 25, the two-axis magnetic-field generator 374 of FIG. 24 is symbolically shown in FIG. 25 as a single-turn coil, but would normally be made as a bundled-conductor coil, as previously described.

The two-axis generator 374 includes the horizontal coil portion 382A, and an other horizontal coil portion 382A, the vertical coil portion 386B and an other vertical coil portion 386B, a front portion 392, a first rear portion 394A, and a second rear portion 394B. The first and second rear portions, 394A and 394B, are connected to positive and negative potentials, as shown, to any suitable source of electrical power.

The coil portions 386A and 386B tend to develop a magnetic field whose poles are vertical, as shown by the vertical axis 376 of FIG. 24. In like manner, the portions 382A and 382B tend to develop a magnetic field whose poles are horizontal, as shown by the horizontal axis 378 of FIG. 24. Therefore, the magnetic-field generator 374 is a two-axis magnetic-field generator.

Figure 26:
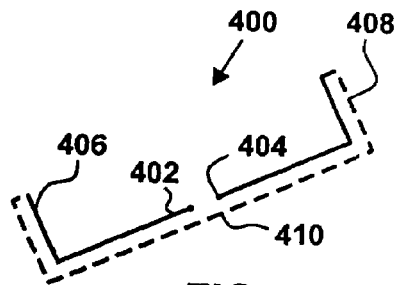
FIG. 26 is a schematic, in perspective form of a single-axis magnetic-field generator for uses, such as a desk of FIG. 27, showing shielded return conductors in dash lines.

Referring now to FIG. 26 a U-shaped magnetic-field generator 400 includes a pair of active back portions 402 with terminals 404 which may be connected to a source of electrical power, a pair of active side portions 406, a pair of magnetically-shielded side portions 408, and a magnetically-shielded back portion 410. Magnetic shielding can be achieved by the use of soft iron sheets, or by any suitable means, not an inventive part of the present invention.

Figure 27:
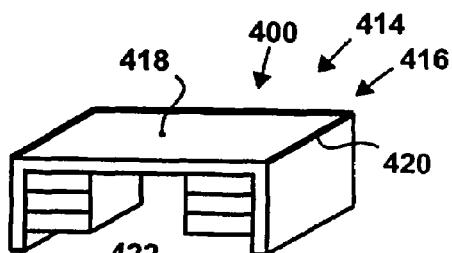
FIG. 27 is a perspective drawing of a magnetic-field-enhancing desk that includes the single-axis magnetic-field generator of FIG. 26, showing a general location of the U-shaped generator by means of heavier outlines of the desk top.

Referring now to FIG. 27, a magnetic-field-enhancing apparatus or a magnetic-field-enhancing desk 414 includes a desk or a desk structure 416, and the U-shaped generator 400 of FIG. 26. The desk 414 includes a top 418, and the location of the U-shaped generator 400 is symbolized by heavier lines along three of four edges 420 of the top 418.

Since the U-shaped generator 400 is open-sided, although the poles of the magnetic-field developed thereby are generally vertical, it is easy to see that the magnetic field will flow forward, thereby providing a magnetic-field-enhanced living space 422 that will engulf a person, not shown, who is using the desk 414.

Referring now to FIGS. 28 and 29, a magnetic-field-enhancing bassinet 428 includes a bassinet 430, and shown only in FIG. 29, one or more of electrical magnetic-field generators 432, 434, 436, and/or 438, or one of two types of permanent-magnet magnetic-field generators that will be discussed subsequently.

The bassinet 428 includes perimetrical sidewalls 440 with a perimetrical top rim 442, and shown only in FIG. 29, a bottom 444 that is inserted into the sidewalls 440, and a perimetrical flange 446 that extends downward from the bottom 444, providing a bottom recess 448. A baby 450 lying on a mattress 452 is spaced away from the sidewalls 440 by a perimetrical pad 454.

If one or more of the electrical magnetic-field generators, 432, 434, 436, and/or 438 are used, a battery 456 may be installed in the bottom recess 448 to provide electrical power.

If the electrical magnetic-field generator 432 is used, it is disposed perimetrically around the sidewalls 440, and is bunched along a line 458 that extends through the baby 450. If the electrical magnetic-field generators 434 and 436 are used, they are disposed perimetrically around the sidewalls 440, and are bunched along lines 460 and 462, respectively. If the electrical magnetic-field generator 438 is used, it is disposed perimetrically around the sidewalls 440, and distributed between the lines 460 and 462.

Referring now to FIG. 30, a domino-shaped permanent magnet 466 has a face that is 1.875 inches (4.76 cm) long and 0.875 inches (22.2 mm) wide, and has a thickness of 0.375 (9.5 mm). As shown, the permanent magnet 466 is magnetized with a single pole of one polarity on one face, and a single pole of an opposite polarity on an opposite face, so that magnetic flux flows as shown by a magnetic flux line 468.

The permanent magnet of FIG. 30 produces a magnetic flux density of 800 gauss on each face, weighs 1.75 ounces (49.6 grams), and will lift forty-one identical permanent magnets. In contrast, the sheets of flexible magnetic material of FIG. 8 will not even stick together.

Referring now to FIG. 31, if two rows 470 of the permanent magnets 466 of FIG. 30 are spaced at a distance 472, a magnetic field will be developed between the magnets, and symmetrically, both above and below, the magnets 466, as indicated by the flux lines 474.

Referring now to FIG. 32, a parallel-bar permanent magnet enhancer 480 includes rows 482A and 482B of the permanent magnets 466 that are spaced apart by a distance 484. The magnets 466 are forcibly and tightly juxtaposed together, and the rows 482A and 482B have equal lengths 486. The North poles of all of the magnets 466 are disposed upwardly, as indicated by the letter "N".

By juxtaposing a plurality of the magnets 466 together to form the rows 482A and 482B, magnetic flux cannot flow around any of ends 488, except for those of magnets 466 that are at the ends of the rows 482A and 482B. A living space 490 is provided that is inside the rows 482A and 482B, and that extends both above and below the rows 482A and 482B.

Referring now to FIG. 33, a closed-ring magnetic-field generator 496 includes the rows 482A and 482B of permanent magnets 466 of FIG. 31. In addition, the closed-ring permanent-magnet generator 496 includes rows 498A and 498B of permanent magnets 466 that are juxtaposed against the rows 482A and 482B, as shown, to form the closed-ring magnetic-field generator 496.

By juxtaposing the rows 498A and 498B against the ends 488 of the rows 482A and 482B of FIG. 32, flow of magnet flux about the ends 488 of FIG. 32 is precluded, and magnetic flux inside the closed-ring magnetic-field generator 496 is increased. However, there is some flux loss at ends 500 of the rows 498A and 498B, as shown by a flux line 502.

Referring now to FIGS. 34 and 35, a magnetic-field-enhancing bassinet, playpen, or bed, or magnetic-field-enhancing apparatus 506 includes a bassinet structure, playpen structure, or bed structure 508, a mattress 510 having a living surface 512, and a magnetic-field generator pad, 514. The magnetic-field generator pad 514 includes an upper surface 516 and a lower surface 518, with a single one of the magnetic poles on respective ones of the surfaces, 516 and 518, as shown. The magnetic-field generator pad 514 is made of flexible magnetic material such as taught in conjunction with FIG. 8.

A magnetic-field-enhanced living space 520 includes a length 522, a width 524, and a height 526 for a person, or living thing, 528 in which an enhancing magnetic field 530 is provided in the living space 520, that when vectorially added to the earth's magnetic field, produces a dc magnetic field that is vectorially greater than the earth's magnetic field, as taught in conjunction with FIG. 3.

Since the magnetic-field generator pad 514 is magnetized with a single North pole on one side and a single South pole on the other side, all of the magnetic flux flows nonreversingly, or unidirectionally, from one side of the pad 514, nonreversingly, or unidirectionally, through the living space 520, in the opposite direction around the pad 514, and unidirectionally into the other side of the pad 514.

Referring now to FIG. 35A, a magnetic-field generator pad 532, that may be used instead of the generator pad 514 of FIGS. 34 and 35, includes edges 534 that are bent upwardly, as shown, to focus the magnetic field. In like manner, referring now to FIG. 35B, a magnetic-field generator pad 536, that may be used instead of the generator pad 514 of FIGS. 34 and 35, includes ends 538 and edges 540 that are both bent upwardly to focus the magnetic field.

Referring now to FIG. 35C, a magnetic-field-enhancing mattress or magnetic-field-enhancing apparatus 544 includes a foam mattress pad 546 and the magnetic-field-generator pad 548 in a cover 550.

Referring now to FIG. 35D, a magnetic-field-enhancing mattress 552 includes the foam mattress pad 546, the magnetic-field-generator pad 548, and the cover 550 of FIG. 35C. In addition, the magnetic-field enhancing mattress 552 includes either two, or four, doubler strips 554 that are also made from flexible magnetic material, such as that used for the tests of FIG. 8, and that are each juxtaposed to an edge 556 of the generator pad 548.

By doubling or tripling the thickness of the pad 548 wherein the strips 554 are placed, the magnetic field is strengthened along the edges 556. Strengthening the magnetic field along the edges 556 increases the magnetic field inward of the edges 556 because the strengthened magnetic field along the edges 556 increases the length of the magnetic path around the pad 548, even as a dam increases depth of water.

Figure 42:
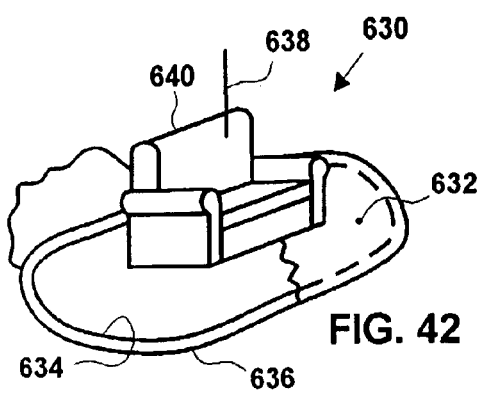
FIG. 42 is a perspective view of a magnetic-field-enhancing carpet that includes a magnetic-field generator in the form of a bundled-loop coil, with seating furniture disposed inside an area circumscribed by the magnetic-field generator.

Referring now to FIG. 36, a magnetic-field-enhancing child car seat or magnetic-field-enhancing apparatus 560 is attached to a vehicle seat 562 in a vehicle 564. A magnetic-field generator 566, as indicated by a phantom line, provides an enhancing magnetic field generally in a direction 568. The magnetic-field generator 566, which may be of the type using the generator coil as shown in FIG. 24, permanent magnets as shown in FIG. 42 or 33, or the enhancer pad as shown in FIGS. 34 and 35, provides an enhancing magnetic field for a child, whether a child's head 570 is in a vertical position, as shown, or in a sleeping position 572 as shown by phantom lines.

Referring now to FIG. 37, a magnetic-field-enhancing cap or Magcap 576 includes a crown-conforming portion 578 and a bill 580. Referring now to FIG. 37A, the Magcap 576 includes an outer fabric layer 582, an inner fabric layer 584, and a magnetic-field generator or magnetic-field-generator pad 586 that is polarized, as shown. Whereas others have taught placing a South magnetic pole proximal to a body or body member for some supposed medical reason, in the Magcap 576, the North pole is placed proximal to the head, so that the magnetic field produced by the magnetic-field generator 586 enhances the earth's dc magnetic field, as shown by a vector 588.

Figure 38A:
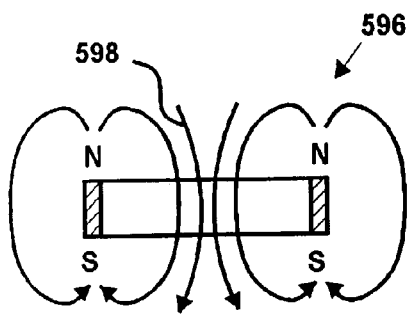
FIG. 38A is a cross-section of the headband of FIG. 38, showing preferred magnetization in which upper and lower edges are magnetized as separate poles.
Figure 38B:
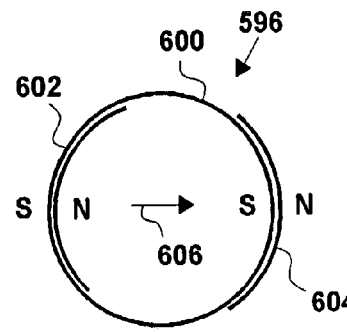
FIG. 38B is a symbolic top view of a magnetic-field generator that may be used in a Magband, a dress belt, a back support, or some other magnetic-field-enhancing apparatus, showing an alternate magnetic pole arrangement.

Referring now to FIGS. 38, 38A, and 38B, in FIG. 38, a person 594 is wearing a magnetic headband, body-member-encircling band, or Magband 596. As shown in FIG. 38A, preferably the Magband 596 is edge magnetized as indicated, thereby providing magnetic flux as shown by flux lines 598, and thereby enhancing the earth's dc magnetic field.

In FIG. 38B, alternate magnetization of the Magband 596 is shown. Portions 600 are not magnetized as indicated by a single line. Portions 602 are magnetized with a North Pole on the inside of the Magband 596, and portions 604 are magnetized with a North Pole on the outside of the Magband 596, thereby providing magnetic flux completely through the Magband as shown by a line 606. Therefore, in addition to providing flow of magnetic flux completely through a head, or body member, 608 of the person 594, the earth's dc magnetic field is vectorially enhanced.

Figure 39:
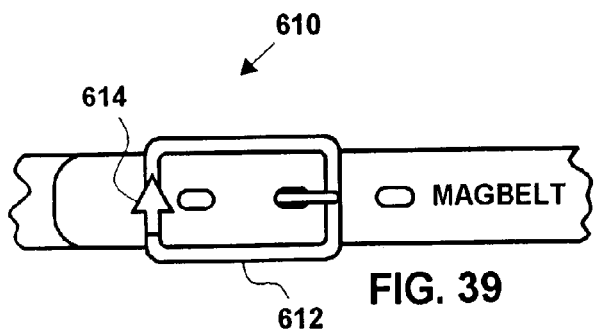
FIG. 39 is a partial elevation of a magnetic-field-enhancing apparatus in the form of a magnetic-field-enhancing belt, Magbelt, whose poles preferably are as shown in FIG. 38A, but that may be as shown in FIG. 38B, showing an up arrow on the buckle for correct use when the pole arrangement of FIG. 38A is used.

Referring now to FIG. 39, a magnetic-field-enhancing belt, body-part-encircling band, or Magbelt, 610 preferably is edge magnetized as taught in conjunction with FIG. 38A, but optionally may be magnetized in accordance with FIG. 38B, with advantages as taught in conjunction with FIGS. 38A and 38B. A buckle 612 includes an up arrow 614 as a guide for correct use when the Magbelt 610 is magnetized in accordance with the teaching of FIG. 38A.

Figure 40:
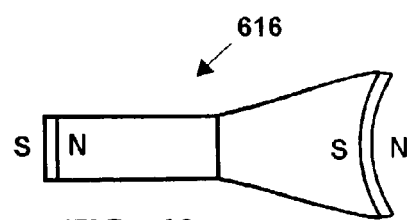
FIG. 40 is a cross-sectional view of magnetic-field-enhancing apparatus in the form of a magnetic-field-enhancing back brace, or a Magbrace whose poles preferably are as shown in FIG. 38A, but may be as shown in FIG. 38B.

Referring now to FIG. 40, a magnetic-field-enhancing back brace, body-part-encircling band, or Magbrace 616, preferably is edge magnetized as taught in conjunction with FIG. 38A, but alternately may be magnetized in accordance with the teaching of FIG. 38B.

Referring now to FIGS. 37-40, the Magcap 576 of FIG. 37, the Magband 596 of FIG. 38, the Magbelt 610 of FIG. 39, and the Magbrace 616 of FIG. 40 each provide a magnetic field that penetrates a body member, that vectorially adds an enhancing magnetic field to the earth's dc magnetic field, thereby providing a magnetic-field-enhanced magnetic field that penetrates a body member.

Figure 41:
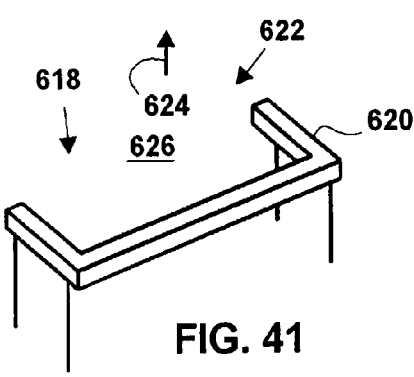
FIG. 41 is a perspective view of a magnetic-field-enhancing carrel in the form of a free-standing railing that uses rows of permanent magnets, such as the rows of FIG. 32, to form a U-shaped magnetic-field generator.
Figure 41A:
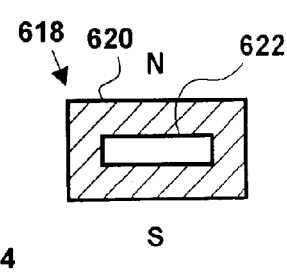
FIG. 41A is a cross-sectional elevation of the free-standing railing of FIG. 41, showing one permanent magnet, of a row of permanent magnets, in one section of the railing.

Referring now to FIGS. 41 and 41A, a magnetic-field-enhancing carrel or magnetic-field-enhancing apparatus 618 of FIG. 41 includes a U-shaped carrel 620 and a magnetic-field generator 622. In FIG. 41A, the magnetic-field generator 622 is shown in cross section with the U-shaped carrel 620. The magnetic-field generator 622 preferably is constructed of domino-shaped magnets 466 of FIG. 30, that are disposed in rows, such as the rows 482A and 482B of FIG. 32. A magnetic field is developed by the magnetic-field-enhancing carrel 618 that generally is vertical, as shown by a vertical axis 624, but slopes outwardly from an open side 626.

Referring now to FIG. 42, a magnetic-field-enhancing carpet, or magnetic-field-enhancing apparatus 630 includes a carpet 632 and a magnetic-field generator 634. The magnetic-field generator 634 is in the form of a bundled coil and is circumferentially disposed with respect to a perimeter 636 of the carpet 632.

The magnetic-field-enhancing carpet 630 provides a magnetic-field-enhanced living space in an area roughly defined by the magnetic-field generator 634 that extends upwardly with magnetic poles being disposed generally along a vertical axis 638, so that a person, not shown, sitting in seating furniture 640 is subjected to an enhanced dc magnetic field. Optionally, the magnetic-field generator 634 is separate from the carpet 632.

Figure 43:
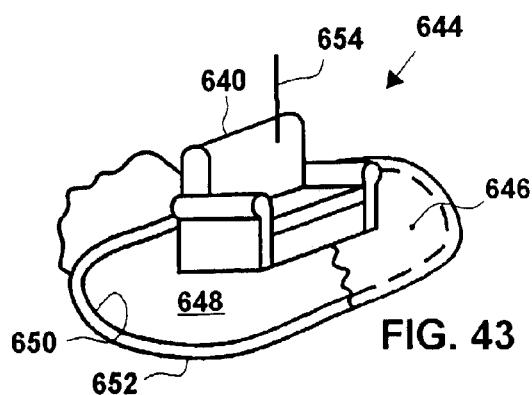
FIG. 43 is a perspective view of a magnetic-field-enhancing carpet that includes a magnetic-field generator in the form of a magnetized sheet of material, and that includes edge enhancement, with seating furniture disposed inside an area circumscribed by the magnetic-field generator.

Referring now to FIG. 43, a magnetic-field enhancing carpet or magnetic-field-enhancing apparatus 644 includes a carpet 646 and a magnetic-field generator 648. The magnetic-field generator 648 is in the form of a pad of magnetized material, with magnetic poles as taught in conjunction with FIGS. 34 and 35. In addition, the magnetic-field generator 648 includes a doubler strip 650 of magnetized material to increase the magnetic field proximal to a periphery 652 of the carpet 646.

The magnetic-field-enhancing carpet 644 provides a magnetic-field-enhanced living space in an area roughly defined by the magnetic-field generator 648 that extends upwardly with magnetic poles being disposed generally along a vertical axis 654, so that a person, not shown, sitting in the seating furniture 640 is subjected to an enhanced dc magnetic field. Optionally, the magnetic-field generator 648 is separate from the carpet 646.

Figure 44:
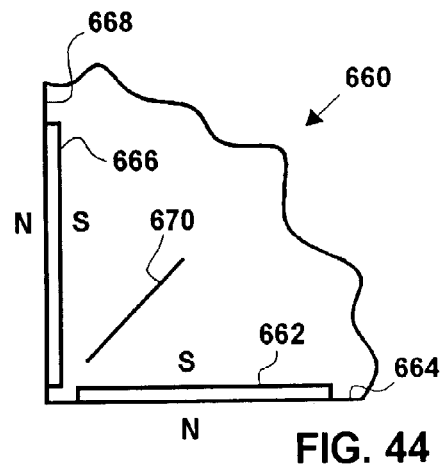
FIG. 44 is a partial front elevation of a magnetic-field-enhancing room that includes two magnetic-field generators, in the form of two magnetized sheets that are disposed at right angles to each other, one being disposed on a floor, and an other being disposed on a wall, whereby an enhancing magnetic field is developed with respect to an axis that is disposed between the two magnetic-field generators.

Referring now to FIG. 44, a magnetic-field-enhancing room or magnetic-field-enhancing apparatus 660 includes a first magnetic-field generator 662 in the form of a magnetized sheet of material that is disposed on a floor 664, and second magnetic-field generator 666 that is disposed in a wall 668. The magnetic-field generators, 662 and 666 are magnetized with magnetic poles as shown, and as taught in conjunction with FIGS. 34 and 35. An enhancing magnetic field is produced whose axis is generally as shown by an inclined axis 670.

Figure 45:
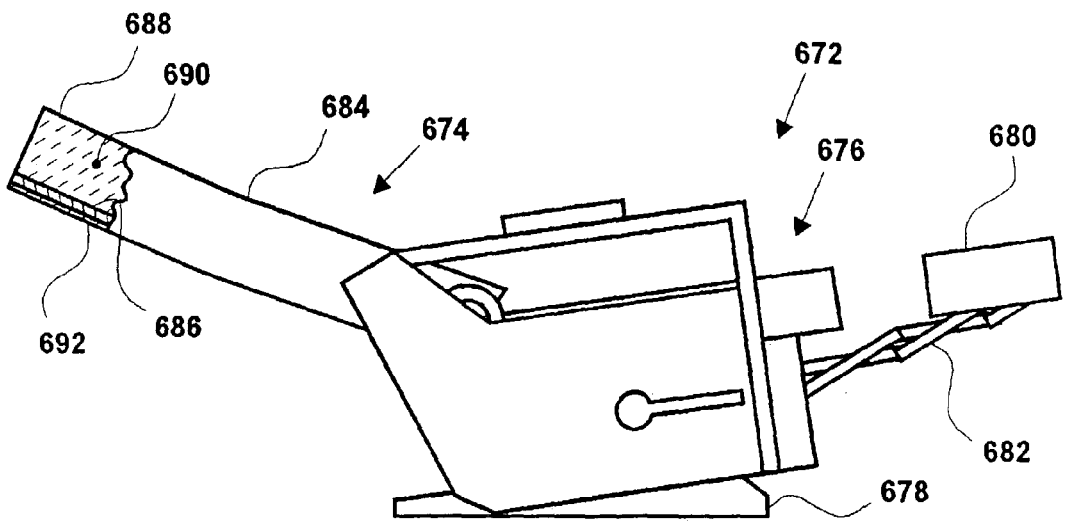
FIG. 45 is a partially cross-sectioned side view of a reclining chair that is extended in the reclining position, with a leg-supporting portion spaced-apart from a seat portion, and with a partial cross-section showing a magnetic field generator in a back portion in the form of a sheet of magnetized material.

Referring now to FIG. 45, a magnetic-field enhancing chair or magnetic-field-enhancing apparatus 672 includes a magnetic-field-enhancing back portion 674, a magnetic-field-enhancing seat portion 676, a structure 678, a leg-support portion 680, and a leg-support extending mechanism 682. The magnetic-field-enhancing back portion 674 includes a back portion 684, and a magnetic-field generator 686 that is in the form of a sheet of magnetized material that may be in the order of 0.125 inches (3.2 mm) thick, and that includes magnetic poles as taught herein.

Figure 45A:
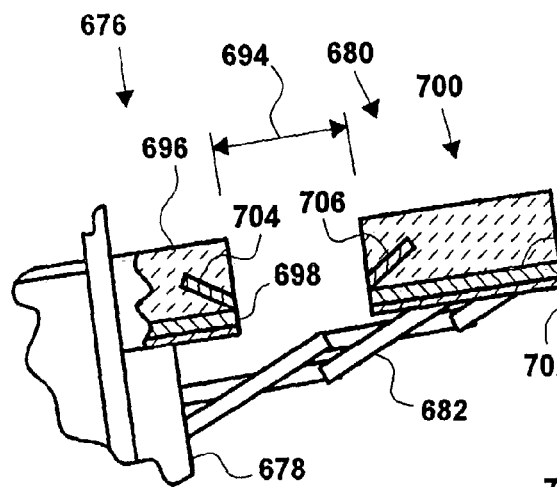
FIG. 45A is an enlarged partial cross-section of the reclining chair of FIG. 45, taken substantially the same as FIG. 45, showing supplementary magnetic-field generators, in the form of sheets of magnetized material for magnetically bridging a gap between a seat and a leg-support portions of the reclining chair.

The back portion 684 includes a cover 688, a sheet of foam rubber 690, and a back board 692, and the magnetic-field generator 686 is disposed between the foam rubber 690 and the back board 692. The magnetic-field-enhancing seat portion 676 is constructed similarly, except as will be described in conjunction with FIG. 45A Referring now to FIG. 45A, a cross-sectioned portion of the magnetic-field enhancing seat 676 is shown with the leg-support portion 680 separated at a distance 694 by the mechanism 682 that connects the leg-support portion 680 to the structure 678. The magnetic-field-enhancing seat portion 676 includes a seat portion 696 and a magnetic-field generator 698 that is in the form of a sheet of magnetized material with magnetic poles as taught herein. In like manner, the magnetic-field-enhancing leg-support portion 680 includes a leg-supporting portion 700 and a magnetic-field generator 702 that is in the form of a sheet of magnetized material with magnetic poles as taught herein.

In addition to the magnetic-field generator 698, the magnetic-field-enhancing seat portion 676 also includes a supplementary magnetic-field generator 704 that is disposed at an angle, as shown. And the magnetic-field-enhancing leg-support portion 680 includes a supplementary magnetic-field generator 706 that is disposed at an angle, as shown.

The supplementary magnetic-field generators, 704 and 706, not only provide supplementary magnetic field, but also, because the supplementary magnetic-field generators, 704 and 706, are inclined at angles, as shown, their magnetic fields bridge the gap of the distance 694, filling the space between the portions 696 and 700 with their own magnetic fields so that a continuous magnetic field is provided by the magnetic-field generators 698 and 702, even though the leg-supporting portion 700 is separated from the seat portion 696 by the distance 694.

Figure 46:
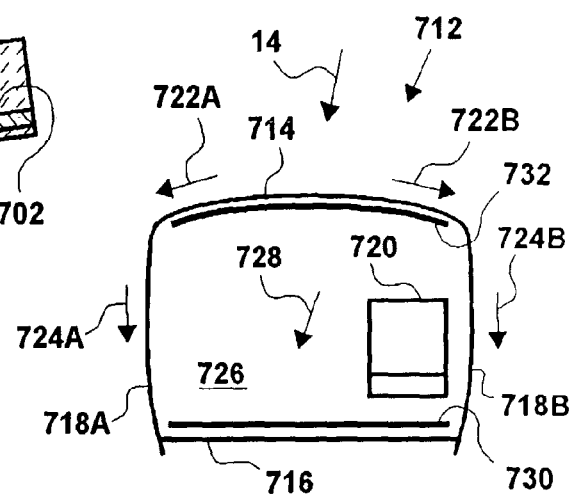
FIG. 46 is cross-sectioned front elevation of a vehicle showing that the steel roof, walls, and floor degrades the earth's dc magnetic field, and showing restoration and/or enhancement of the dc magnetic field by the use of floor and roof magnetic-field generators.

Referring now to FIG. 46, a magnetic-field-restoring vehicle or magnetic-field-enhancing vehicle 712 includes a steel roof 714, a steel floor 716, steel walls 718A and 718B that connect the steel roof 714 to the steel floor 716, and a driver's seat 720. The vehicle 712 is facing West, so the steel wall 718A is to the North, and orientation of the North pole is represented by the vector 14.

Since the magnetic reluctance of steel is in the order of a thousand times lower than that of air, a portion of the magnetic flux of the earth's dc magnetic flux flows transversely through the material of the steel roof 714, as illustrated by vectors 722A and 722B, and downwardly through the steel walls 718A and 718B, as illustrated by vectors 724A and 724B, thereby degrading the earth's dc magnetic field in an interior 726 of the vehicle 712.

A remaining portion of the earth's dc magnetic field flows downwardly through the steel roof 714, downwardly through the interior 726, and through the steel floor 716, as illustrated by a vector 728. The vector 728 is shorter than the vector 14 to illustrate the fact that the earth's dc magnetic field is degraded by steel construction of the vehicle 712.

While it is logical to assume that degradation of the earth's dc magnetic field will vary in accordance with individual design parameters of various makes and models of vehicles, measurements with a gaussmeter indicate an average degradation of fifty percent. Therefore, an operator, not shown, sitting on the seat 720, and passengers, not shown, are disposed in an ambient magnetic field that has been degraded approximately fifty percent by steel construction of the vehicle 712.

While it would be difficult to measure the flow of magnetic flux downwardly through the walls 718A and 718B, flow of magnetic flux through the walls 718A and 718B can be illustrated by the fact that a compass will point to the walls 718A and 718B if the vehicle 712 is oriented in a North-South direction.

Continuing to refer to FIG. 46, a first magnetic-field generator, first magnetized sheet, or first magnetized pad, 730 is disposed proximal to the steel floor 716 generally in a floormat position. A second magnetic-field generator, second magnetized sheet, or second magnetized pad, 732 is disposed proximal to the steel roof 714 generally in a headliner position. While either of the magnetic-field generators, 730 or 732, will vectorially increase the vector 728, using both magnetic-field generators, 730 and 732, is preferred, since it produces the greatest, and most uniform, increase.

If the vehicle 712 is made of steel, as described, then adding the magnetic-field generators 730 and 732 make the vehicle 712 either a magnetic-field-restoring vehicle or a magnetic-field-enhancing vehicle, depending upon the strength of the magnetic field that is generated. However, if the vehicle 712 is not made of magnetic material, adding the magnetic-field generators 730 and 732 makes the vehicle 712 a magnetic-field-enhancing vehicle. Either way, occupants, not shown, of the vehicle 712, travel in a more healthful magnetic field.

Figures 47A, 47B, 47C, 47D:
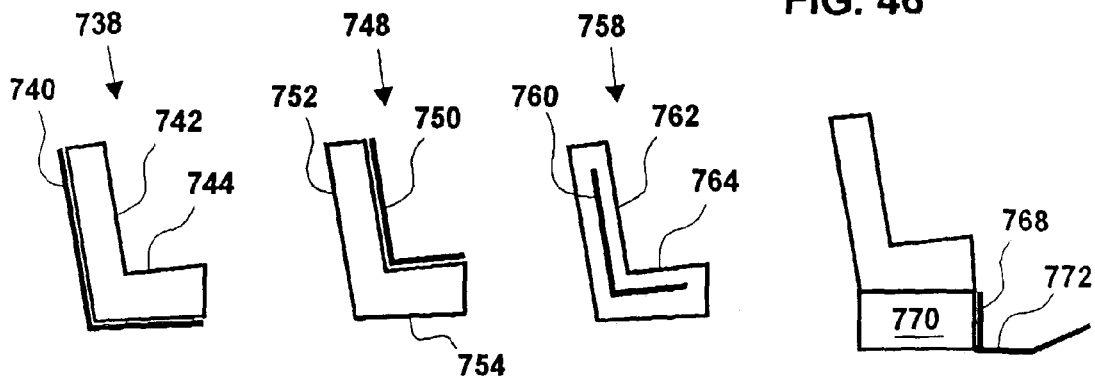
FIG. 47A is a side elevation of a first magnetic-field-enhancing captains chair that is usable in a vehicle, such as the vehicle of FIG. 46, that includes a magnetic-field generator on a back and under a seat of the captains chair.
FIG. 47B is a side elevation of a second magnetic-field-enhancing captains chair that is usable in a vehicle, such as the vehicle of FIG. 46, that includes a magnetic-field generator in front of a back and on top of a seat of the captains chair.
FIG. 47C is a cross-sectioned side elevation of a third magnetic-field-enhancing captains chair that is usable in a vehicle, such as the vehicle of FIG. 46, that includes a magnetic-field generator that is built into a back and into a seat of the captains chair.
FIG. 47D is a cross-sectioned side elevation of a magnetic-field-enhancing base and a magnetic-field-enhancing floor mat for use with the magnetic-field-enhancing captains chairs of FIGS. 47A, 47B, and 47C, and that extend a respective one of the magnetic-field generators down to a floor of a vehicle and forward under feet and legs of a person.

Referring now to FIG. 47A, a magnetic-field-enhancing vehicle chair or magnetic-field-enhancing apparatus 738 includes a magnetic-field generator 740 that is in the form a magnetized sheet, that extends downwardly behind a back 742 of forwardly the chair 738 and under a seat 744.

Referring now to FIG. 47B, in a second embodiment, a magnetic-field-enhancing vehicle chair or magnetic-field-enhancing apparatus 748 includes a magnetic-field generator 750 that is in the form a magnetized sheet, that extends downwardly in front of a back 752 of the chair 748 and forwardly on top of a seat 754.

Referring now to FIG. 47C, in a third embodiment, a magnetic-field-enhancing vehicle chair or magnetic-field-enhancing apparatus 758 includes a magnetic-field generator 760 that is in the form a magnetized sheet, and that extends downwardly-inside a back 762 and forwardly inside a seat 764 of the chair 758.

Referring now to FIGS. 47A-47D, and more particularly to FIG. 47D, in a variation that may be used with any of the magnetic-field-enhancing vehicle chairs 47A-47C, a magnetic-field generator 768, that is in the form of a magnetized pad, extends downwardly in front of a seat pedestal 770. In addition, optionally an other magnetic-field generator 772, that is in the form of a floor mat, may be used in conjunction with any of the magnetic-field-enhancing vehicle chairs 47A-47C.

While construction details have not been shown or described in conjunction with FIGS. 47A-47D, it should be apparent to one skilled in the art that any conceivable construction or method of attachment can be employed without departing from the scope of the disclosed invention.

With regard to vehicles, such as shown and described in conjunction with FIG. 46, the cabs and sleeping quarters of trailer tractors are commonly constructed of aluminum, so that the earth's dc magnetic field is not degraded in either the cab of the tractor or in the operator's sleeping quarters. However, the present invention is useful in providing an enhanced dc magnetic field, both in the cab, and in sleeping quarters.

For instance, extending the magnetic-field generators 730 and 732 back into sleeping quarters, not shown, provides a magnetic-field-enhancing bedroom. Alternately, a magnetic-field-enhancing bed, such as the magnetic-field-enhancing bed 506 of FIGS. 34 and 35, may be used in a trucker's sleeping quarters, or in any other living space used for sleeping.

Referring again to FIG. 43, the magnetic-field generator 648 may be enlarged to cover an entire floor of a room, or enlarged to cover an entire building, or be used in magnetic-field-enhancing vehicles, such as trains or other mass transportation vehicles. The magnetic field generators, such as the magnetic-field generator 648, may be constructed of and laid as tiles, or may be laid under a carpet and carpet pad.

In summary, the present invention produces a restored and/or enhanced dc magnetic field in a living area, in an entire living thing, or in a body member of a living thing. That is, various embodiments of the present invention provide dc magnetic-field enhanced living spaces for entire living things. Other embodiments are worn on the body, and therefore provide restored or enhanced dc magnetic fields in selected body portions.

The present invention can be used: to enhance the earth's dc magnetic field beyond its present time-degraded magnitude; to restore, and optionally to enhance, a healthy dc magnetic field when the earth's dc magnetic field has been degraded by an ac magnetic field; to restore and/or to enhance a healthy dc magnetic field in geographical areas in which the earth's dc magnetic field has been degraded by a natural geological formation; and to restore and/or enhance a normal dc magnetic field when the earth's dc magnetic field has been degraded in a man-made structure, such as a vehicle.

With regard to environmental ac magnetic fields, vector addition of an environmental ac magnetic field with earth's dc magnetic field commonly produces a cyclically-fluctuating dc magnetic field whose cyclic minimum is less than the earth's magnetic field and, therefore, insufficient for healthy cell communication.

However, in the present invention vector addition of an enhancing dc magnetic field, the earth's dc magnetic field, and an environmental ac magnetic field produces a cyclically-fluctuating dc magnetic field whose cyclic minimum is greater than the earth's dc magnetic field, thereby providing a dc magnetic field whose magnitude is sufficient for healthful cell communication, and thereby reducing, or even obviating, the deleterious effects of environmental ac magnetic fields.

With regard to geographical areas, in some geographical areas, natural geological formations of magnetic material cause the earth's dc magnetic field to detour underground, or around those geographical areas, thereby degrading the dc magnetic field. The present invention may be used to restore the dc magnetic field to the magnitude experienced in other geographical areas, or to enhance the earth's dc magnetic field above its present time-degraded magnitude.

With regard to man-made structures, some man-made structures, including vehicles such as cars and vans, and other vehicles constructed of steel, seriously degrade the earth's dc magnetic field. This is especially serious when both driver and passengers are subjected to degraded magnetic fields for long hours.

The enhancing magnetic fields used to practice the present invention may be as low as 0.1 gauss, and as high as, or higher than, 5.0 gauss, and may be at any angle to the earth's dc magnetic field, or at any angle to an ac magnetic field, and in any plane that results in a dc magnetic field that is greater than the earth's dc magnetic field.

Enhancing magnetic fields, as taught herein, may be generated electromagnetically, or permanent magnets may be used in any suitable shape, size, number and/or combination to generate enhancing magnetic fields. However, sheets of magnetized material are preferred for many embodiments.

Obviously, an enhancing magnetic field cannot be an ac magnetic field. Instead, it must be a dc magnetic field. Further, it must provide a nonreversing, or unidirectional, magnetic field in the living area in which the dc magnetic field is to be enhanced or restored. That is, the magnetic flux must flow in a nonreversing direction in the living area in which the magnetic flux density is to be enhanced.

The enhancing magnetic field cannot be developed by a plurality of spaced-apart permanent magnets, as has been used in conventional magnetic mattresses, since, as illustrated in FIG. 30, spaced-apart permanent magnets each develop an omnidirectional magnetic field that flows around each magnet. That is, spaced-apart permanent magnets, as used in conventional magnetic mattresses, generate magnetic fields that flow in all directions in a sleeping space above the mattress, and in all directions into a person sleeping on the mattress. Therefore, spaced-apart permanent magnets could not possibly be used to enhance the earth's dc magnetic field in a living space, or to restore a normal dc magnetic field in a living space that has been degraded by an ac magnetic field.

However, as is well-known to those skilled in the art, all of the magnetic flux of a coil flows axially, and nonreversingly or unidirectionally, out one end of the coil, reverses directions by curving outwardly, flows toward the opposite end of the coil, reverses directions by curving inwardly, and flows nonreversingly, or unidirectionally, into an other end of the coil. Therefore, to enhance the earth's dc magnetic field, or restore a normal dc magnetic field in a living space, the living space must be disposed in the portion of the generated magnetic field that is unidirectional.

In like manner, when a permanent magnet has a single pole on each of two faces, all of the magnetic flux flows nonreversingly, or unidirectionally, from one face, reverses directions by curving outwardly, and flows unidirectionally into the other face. Therefore, to enhance the earth's dc magnetic field, or restore a normal dc magnetic field in a living space, the living space must be disposed in the portion of the generated magnetic field that is unidirectional.

The material used for the tests of FIG. 8 has an MGOe of 0.7, was manufactured by Magnet Technology, Inc. of Lebanon, Ohio, and was magnetized as taught herein. In a test using a spliced sheet 48.0 inches (121.9 cm) wide, 72.0 inches (182.9 cm) long, and 0.060 inches (1.524 mm) thick, magnetic fields of 0.90, 0.78, 0.62, and 0.49 gauss were generated at heights of 12.0, 16.0, 20.0, and 24.0 inches (30.5 cm, 40.6 cm, 50.8 cm, and 61.0 cm) from the magnetized sheet, respectively.

With regard to sheets of magnetic material used in magnetic-field-enhancing apparatus taught herein, it should be understood that any material that may be magnetized with a single magnetic pole of one polarity on one face, and a single pole of an opposite polarity on another face, whether it be a structural material, or a material added for the purpose of providing an enhancing magnetic field, may be used to magnetically enhance any of the living spaces taught herein, or any other living space, whether the magnetized material is used under the living space, at a side of the living space, above the living space, on opposite sides of the living space, or any other suitable combination.

That is, the present invention includes magnetizing a sheet of magnetic material in a manner in which one side will function substantially as a single North magnetic pole and an other side will function substantially as a single South magnetic pole. While it is preferable that sheets of magnetic material be magnetized with an exclusive North pole on one side, and an exclusive North pole on the other side, it should be understood that gaps of non-magnetized material, or even inclusions of areas with reverse magnetization are within the scope of the present invention, as long as an enhancing dc magnetic field is generated in a living space.

Further, while it may be preferable to magnetize a single sheet of magnetic material, the invention may be practiced by use of tiles or elongated strips, and the tiles or strips may be either closely juxtaposed or spaced apart as long as an enhancing dc magnetic field is provided in a living space. The tiles or strips may be placed under or between objects, spliced together, fastened together with Velcro, fastened together with a slide-fastener, vulcanized, or merely placed into position, as long as an enhancing dc magnetic field is generated in a living space.

Although apparatus and method of the present invention has focused on providing a more healthful living environment, as opposed to providing therapeutic apparatus and method, the apparatus and method taught herein may be used, at various gauss intensities, for therapeutic treatment by immersing a patient's entire body, or an entire living thing, into a living space which may be above a bed, a special therapeutic device, a portion of a room, a room, or an entire building, for periods of time that may range from a portion of an hour to days or even weeks.

While body-attached and mattress-pad-inserted magnets are being sold by others that induce magnetic flux intensities of up to approximately 1400 gauss into human flesh for the purpose of magnetic therapy, the present invention uses magnetic fields in a more natural way. In the present invention, a magnetic flux density is provided that is in the natural range used by, or usable by, the human body, to enhance cell communication.

That is, while many teach the use of magnets to cure various diseases by applying magnetic fields of up to 1400 gauss to surface portions of the human body or to surface portions of animals, the present invention generates magnetic fields that penetrate entire living areas. And the magnetic poles of the generated magnetic fields are oriented in predetermined relationships to the earth's dc magnetic field, so that the generated magnetic fields vectorially add to the earth's dc magnetic field. So that, entire bodies of humans or other living things are immersed in an enhanced magnetic field, thereby promoting cell communication and general good health.

Even in embodiments of the present invention wherein magnetic-field generators are body-worn, magnetic fields are generated at moderate gauss levels, and orientation of the magnetic poles in relation to a body member of a body member, or according to a theory that a particular magnetic pole provides the greatest healing power. Instead, in the present invention, poles of body-worn magnetic-field generators are disposed in a particular relationship to the earth's dc magnetic field. A magnetic pole orientation is chosen that vectorially increases the magnitude of the earth's dc magnetic field, thereby providing an enhanced dc magnetic field.

Continuation-in-part of U.S. patent application Ser. No. 09/336,271, filed Jun. 18, 1999, which issued as U.S. Pat. No. 6,203,486 on Mar. 20, 2001, Continuation-in-part of U.S. patent application Ser. No. 09/755,697, filed Jan. 5, 2001, and Provisional Patent Application No. 60/254,739, filed Dec. 11, 2000, are all incorporated herein by reference thereto.

While specific apparatus and method have been disclosed in the preceding description, it should be understood that these specifics have been given for the purpose of disclosing the principles of the present invention, and that many variations thereof will become apparent to those who are versed in the art. Therefore, the scope of the present invention is to be determined by the appended claims, and without regard to any numbers that may be parenthetically inserted in any of the claims.

What is claimed is:

1. A method for permeating an entire living thing with a dc magnetic field that is greater than an ambient dc magnetic field which comprises:
   a) generating a dc magnetic field that permeates a living space with a unidirectional dc magnetic field having a magnetic flux density that is greater than 0.1 gauss;
   b) vectorially adding said unidirectional dc magnetic field to said ambient dc magnetic field in said living space;
   c) said vectorially adding step comprises producing a dc magnetic field vector in said living space that is greater than either said unidirectional dc magnetic field or said ambient dc magnetic field; and
   d) disposing said living thing in said living space.

2. A method as claimed in claim 1 in which said generating and vectorially adding steps comprise:
   a) magnetizing a sheet of magnetic material in a manner in which one side functions substantially as a single North magnetic pole and an other side functions substantially as a single South magnetic pole;
   b) disposing said magnetized sheet proximal to said living space; and
   c) selectively orienting said magnetic poles of said magnetized sheet with respect to said ambient dc magnetic field.

3. A method as claimed in claim 1 in which said generating and vectorially adding steps comprise:
   a) magnetizing a sheet of magnetic material in a manner in which one side functions substantially as a single North magnetic pole and an other side functions substantially as a single South magnetic pole;
   b) increasing a magnetic flux density along an edge of said magnetized sheet; and
   c) selectively orienting said magnetic poles of said magnetized sheet with respect to said ambient dc magnetic field.

4. A method as claimed in claim 1 in which said generating and vectorially adding steps comprise:
   a) magnetizing a first sheet of magnetic material in a manner in which one side functions substantially as a single North magnetic pole and an other side functions substantially as a single South magnetic pole;
   b) magnetizing a second sheet of magnetic material in a manner in which one side functions substantially as a single North magnetic pole and an other side functions substantially as a single South magnetic pole;
   c) placing said magnetized sheets with edges spaced-apart;
   d) increasing a magnetic flux density proximal to one of said spaced-apart edges; and
   e) selectively orienting said magnetic poles of said magnetized sheets with respect to said ambient dc magnetic field.

5. A method as claimed in claim 1 in which said generating and vectorially adding steps comprise:
   a) sizing a sheet of magnetic material in accordance with a sleeping surface of a mattress;
   b) magnetizing said sheet of magnetic material in a manner in which one side functions substantially as a single North magnetic pole and an other side functions substantially as a single South magnetic pole;
   c) disposing said magnetized sheet in a plane that is parallel to said sleeping surface; and
   d) selectively orienting said magnetic poles of said magnetized sheet with respect to said ambient dc magnetic field.

6. A method as claimed in claim 1 in which said generating and vectorially adding steps comprise:
   a) sizing a sheet of magnetic material in accordance with a sleeping surface of a mattress;
   b) magnetizing said sheet of magnetic material in a manner in which one side functions substantially as a single North magnetic pole and an other side functions substantially as a single South magnetic pole;
   c) disposing said magnetized sheet under said sleeping surface; and
   d) selectively orienting said magnetic poles of said magnetized sheet with respect to said ambient dc magnetic field.

7. A method as claimed in claim 1 in which said generating and vectorially adding steps comprise:
   a) sizing a sheet of magnetic material in accordance with a sleeping surface of a mattress;
   b) magnetizing said sheet of magnetic material in a manner in which one side functions substantially as a single North magnetic pole and an other side functions substantially as a single South magnetic pole;
   c) disposing said magnetized sheet within upper and lower surfaces of said mattress; and
   d) selectively orienting said magnetic poles of said magnetized sheet with respect to said ambient dc magnetic field.

8. A method as claimed in claim 1 in which said generating and vectorially adding steps comprise:
   a) conforming a coil of wire into a relationship with said living space that is generally perimetrical;
   b) electrically energizing said coil of wire with a dc electrical current; and
   c) selecting a polarity of said dc electrical current.

9. A method as claimed in claim 1 in which said generating and vectorially adding steps comprise:
   a) conforming a coil of wire into a perimetrical relationship with a mattress that includes a sleeping surface;
   b) electrically energizing said coil of wire with a dc electrical current; and
   c) selecting a polarity of said dc electrical current.

10. A method as claimed in claim 1 in which said generating and vectorially adding steps comprise:
    a) conforming a coil of wire generally to a perimeter of a mattress;
    b) integrating said coil of wire into said mattress;
    c) electrically energizing said coil of wire with a dc electrical current; and
    d) selecting a polarity of said dc electrical current.

11. A method as claimed in claim 1 in which said generating and vectorially adding steps comprise:
    a) placing a coil of wire around a building;

b) energizing said coil of wire with a dc electrical current; and c) selecting a polarity of said dc electrical current.

12. A method as claimed in claim 1 in which said generating and vectorially adding steps comprise:
   a) placing a coil of wire around a room;
   b) energizing said coil of wire with a dc electrical current; and
   c) selecting a polarity of said dc electrical current.

13. A method as claimed in claim 1 in which said generating and vectorially adding steps comprise:
   a) placing a coil of wire around an article of furniture;
   b) energizing said coil of wire with a dc electrical current; and
   c) selecting a polarity of said dc electrical current.

14. A method as claimed in claim 1 in which said generating step comprises generating said dc magnetic field in a carrel.

15. A method for restoring a normal dc magnetic field vector in a living space wherein earth's dc magnetic field has been degraded by vectorial addition of an ac magnetic field, which method comprises:
   a) generating a dc magnetic field that permeates said living space with a unidirectional dc magnetic field having a magnetic flux density that is greater than 0.1 gauss;
   b) vectorially adding said unidirectional dc magnetic field to said degraded dc magnetic field; and
   c) said vectorially adding step comprises producing a dc magnetic field vector that is greater than either said unidirectional dc magnetic field or said degraded dc magnetic field, and that is equal to, or greater than, said normal dc magnetic field vector.

16. A method as claimed in claim 15 in which said generating and vectorially adding steps comprise:
   a) magnetizing a sheet of magnetic material in a manner in which one side functions substantially as a single North magnetic pole and an other side functions substantially as a single South magnetic pole;
   b) disposing said magnetized sheet proximal to said living space; and
   c) selectively orienting said magnetic poles of said magnetized sheet with respect to said earth's dc magnetic field.

17. A method as claimed in claim 15 in which said generating and vectorially adding steps comprise:
   a) conforming a coil of wire into a relationship with said living space that is generally perimetrical;
   b) electrically energizing said coil of wire with a dc electrical current; and
   c) selecting a polarity of said dc electrical current.

18. A method for providing an enhanced dc magnetic field above a sleeping surface, which method comprises:
   a) generating a unidirectional dc magnetic field;
   b) said generating step comprises magnetizing a sheet of magnetic material in a manner in which one side functions substantially as a single North magnetic pole and an other side functions substantially as a single South magnetic pole;
   c) sizing said magnetized sheet to correspond to said sleeping surface;
   d) disposing said magnetized sheet proximal to said sleeping surface; and
   e) said disposing step comprises orienting said single North magnetic pole of said magnetized sheet proximal to earth's South magnetic pole.

19. A method as claimed in claim 18 in which said disposing step further comprises disposing said sheet of magnetized material under a mattress.

20. A method as claimed in claim 18 in which said disposing step further comprises integrating said sheet of magnetized material into a mattress.

21. A method as claimed in claim 18 in which said sizing step comprises splicing.

22. A method for permeating a portion of a body member with a dc magnetic field, which method comprises:
   a) sizing a strip of magnetic material that includes two sides and two edges that connect said sides;
   b) magnetizing said strip of magnetic material in a manner in which one of said edges functions substantially as a single North magnetic pole and an other of said edges functions substantially as a single South magnetic pole;
   c) disposing said magnetized strip around a portion of a circumference of said body member; and
   d) disposing said single North magnetic pole proximal to earth's South magnetic pole.

23. A method for providing an enhanced unidirectional dc magnetic field which comprises:
   a) generating a unidirectional dc magnetic field;
   b) said generating step comprises magnetizing a sheet of magnetic material in a manner in which one side functions substantially as a single North magnetic pole and an other side functions substantially as a single South magnetic pole;
   c) disposing said North pole proximal to a South pole of earth's magnetic field; and
   d) placing said magnetized sheet onto a horizontal surface.

24. A method for providing an enhanced unidirectional dc magnetic field above a seating portion of a seat which comprises:
   a) magnetizing a sheet of magnetic material in a manner in which one side functions substantially as a single North magnetic pole and an other side functions substantially as a single South magnetic pole;
   b) disposing a first portion of said magnetized material proximal to, and generally parallel to, a back portion of a seat;
   c) disposing a second portion of said magnetized material proximal to, and generally parallel to, a seating portion of said seat; and
   d) disposing a North pole of said second portion proximal to a South pole of earth's magnetic field.

25. A method as claimed in claim 24 in which said method further comprises making said magnetized material an integral part of said back and seat portions.

26. A method as claimed in claim 24 in which said method further comprises disposing said second portion downward in front of said seat portion.

27. A method as claimed in claim 24 in which said method further comprises disposing said second portion downward in front of said seat portion and forward from said seat portion.

* * * * *